United States Patent
Cox et al.

(10) Patent No.: US 10,624,885 B2
(45) Date of Patent: Apr. 21, 2020

(54) METHOD FOR PRODUCING BENZAZOLOQUINOLIUM (BQS) SALTS AND USING THE BIOLOGICAL ACTIVITY OF THE COMPOSITION

(71) Applicant: Sistema Universitario Ana G. Mendez, Inc., San Juan, PR (US)

(72) Inventors: Osvaldo Cox, Humacao, PR (US); Beatriz Zayas, San Juan, PR (US)

(*) Notice: Subject to any disclaimer, the term of this patent is extended or adjusted under 35 U.S.C. 154(b) by 0 days.

(21) Appl. No.: 15/895,783

(22) Filed: Feb. 13, 2018

(65) Prior Publication Data

US 2018/0214441 A1 Aug. 2, 2018

Related U.S. Application Data

(63) Continuation-in-part of application No. 14/857,500, filed on Sep. 17, 2015, now Pat. No. 9,889,128.

(60) Provisional application No. 62/051,875, filed on Sep. 17, 2014, provisional application No. 62/121,157, filed on Feb. 26, 2015.

(51) Int. Cl.
*A61K 31/4745* (2006.01)
*A61P 35/00* (2006.01)

(52) U.S. Cl.
CPC .......... *A61K 31/4745* (2013.01); *A61P 35/00* (2018.01)

(58) Field of Classification Search
CPC .............................. A61K 31/4745; A61P 35/00
See application file for complete search history.

(56) References Cited

U.S. PATENT DOCUMENTS 9,889,128 B2 * 2/2018 Cox ................... A61K 31/4745
2012/0129882 A1 * 5/2012 Zayas ................. C07D 471/04
514/285

OTHER PUBLICATIONS

Vivas-Mejia et al. Molecular and Cellular Biochemistry, 1997, vol. 7, pp. 69-77 (Year: 1997).*
Vivas-Mejia et al. Molecular and Cellular Biochemistry, 1998, vol. 178, pp. 203-212 (Year: 1998).*
Sausville et al. Cancer Research, 2006, vol. 66, pp. 3351-3354 (Year: 2006).*
Johnson et al. British J. of Cancer, 2001, 84(10):1424-1431 (Year: 2001).*
Chaudhary et al. Journal of Pharmaceutical Negative Results, Jul.-Dec. 2011, vol. 2, No. 2, pp. 62-68 (Year: 2011).*
Leblanc R., Dickson J., Brown T., Stewart M., Pati H.N., Vanderveer D., Arman H., Harris J., Pennington W., Holt H.L. Jr., Lee M.; Synthesis and cytotoxicity of epoxide and pyrazole analogs of the combretastatins; Bioorg Med Chem. Nov. 1, 2005;13(21): 6025-34. PubMed PMID: 16055334.
Cox, O., Velez, C., Kumar, V., Malhotra, S. V., Rivera, L. A., Hernandez, W. J., Martinez, J. R., Cordero, M., & Zayas, B.; Synthesis of and Biological Study of 7-Benzyl-3-aminobenzimidazo[3,2-a]quinolinium Chloride (ABQ-48: NSC D-763307) and 7-benzyl-3-nitrobenzimidazo[3,2-a]quinolinium Chloride (NBQ 48: NSC D-763303); Curr. Bioact. Compd. 10, 286-291. DOI: 10.2174/15734072106661411262043555.
Bellotto, S., Reuter, R., Heinis, C., & Wegner, H. A.; Synthesis and Photochemical Properties of Oligo-ortho-azobenzenes; 2011 J. Org. Chem. 76, 9826-9834.
Chang, C.S., Liu, J.F., Lin, H.J., Lin, C.D., Tang, C.H., Lu, D.Y., Sing, Y.T., Chen, L.Y., Kao, M.C., Kuo, S.C., & Lai, C.H.; Synthesis and bioevaluation of novel 3,4,5-trimethoxybenzylbenzimidazole derivatives that inhibit Helicobacter pylori-induced pathogenesis in human gastric epithelial cells; 2012 Eur. J. Med. Chem. 48, 244-254.
Wlodkowic D., Skommer J., Darzynkiewicz Z.; Cytometry of apoptosis. Historical perspective and new advances; Exp Oncol. Oct. 2012; 34(3):255-62. Review. PubMed PMID: 23070010; PubMed Central PMCID: PMC3476471.
Wlodkowic D., Telford W., Skommer J., Darzynkiewicz Z.; Apoptosis and beyond: cytometry in studies of programmed cell death; Methods Cell Biol. 2011; 103:55-98. doi: 10.1016/B978-0-12-385493-3.00004-8. Review. PubMed PMID: 21722800; PubMed Central PMCID: PMC3263828.
Kitazumi I., Tsukahara M.; Regulation of DNA fragmentation: the role of caspases and phosphorylation; FEBS J. Feb. 2011;278(3):427-41. doi: 10.1111/j.1742-4658.2010.07975.x. Epub Dec. 23, 2010. Review. PubMed PMID: 21182594.
Kroemer G., Galluzzi L., Brenner C.; Mitochondrial membrane permeabilization in cell death; Physiol Rev. Jan. 2007;87(1):99-163, Review, PubMed PMID: 17237344.

* cited by examiner

*Primary Examiner* — James D. Anderson
(74) *Attorney, Agent, or Firm* — Eugenio J. Torres-Oyola; Victor M. Rodriguez-Reyes; Rafael Rodriguez-Muriel

(57) ABSTRACT

Disclosed is the synthesis procedure for benzazolo[3,2-a]quinolinium chloride salts and the inclusion of chloro-substituent, amino-substituent, and nitro-substituent resulting in several compounds. The compounds are further used as markers due to their fluorescent properties including in hypoxic environments.
This disclosure further describes anti-cancer screening of two BQS, namely, 7-benzyl-3-aminobenzimidazo[3,2-a]quinolinium chloride (ABQ-48: NSC D-763307) and the corresponding 7-benzyl-3-nitrobenzimidazo[3,2-a]quinolinium chloride (NBQ 48: NSC D-763303).

21 Claims, 41 Drawing Sheets

| Compound | X | $R_1$ | $R_2$ |
|---|---|---|---|
| ABQ-48 | $NCH_2C_6H_5$ | 3-$NH_2$ | H |
| ABQ-91 | S | 3-$NH_2$ | 10-Me |
| ABQ-2 | S | 3-$NH_2$ | H |
| ABQ-25 | S | 3-$NH_2$ | 9-OMe |
| ABQ-50 | N-n-Butyl | 3-$NH_2$ | H |
| ABQ-74 | S | 3-$NH_2$ | 8,9-$C_4H_4$ |
| ABQ-97 | S | 3-$NH_2$ | 10-OMe |
| ABQ84 | S | 3-$NH_2$ | 8,9-di-OMe |
| ABQ-47 | NMe | 3-$NH_2$ | H |
| ABQ-49 | NiPr | 3-$NH_2$ | H |
| ABQ-59 | $NCH=CHCH_3$ | 3-$NH_2$ | H |
| ABQ-60 | c-$C_5H_9$ | 3-$NH_2$ | H |
| ABQ-121 | S | 3-$NH_2$ | 10-OMe |
| ABQ-122 | S | 2-$NH_2$ | 9-OMe |

| Solvent | CH₃CN | PBS 7.4 |
|---|---|---|
| Absorbance | | |
| $\lambda_{max}$ (nm) [log ε] | 266[4.18], 333[3.83], 348[3.76], 384 [3.15] | 259[4.47], 330[4.11], 342[4.07], 371[3.66] |
| Emission | | |
| $\lambda_{max}$ (nm) | 426, 521 | 413, 525 |
| $E_s$ (Kcal/mol) KJ/mol | 73.6 and 62.2 308 and 260 | 75 and 64 312 and 267 |
| Stoke's shift (cm⁻¹) | 3968[a] 5809[b] | 4210c 7763[d] |
| $\varphi_F$ | 0.21 ± 0.02 | 0.071 ± 0.007 |

Figure 3

| CBQ | $\lambda_{abs}$ (nm) | $\lambda_{emission}$ | $\varphi_f$ |
|---|---|---|---|
| 76 | 378 | 418 | 0.22 |
| 82 | 380 | 424 | 0.19 |
| 108 | 371 | 439 | 0.20 |
| 113 | 375 | 468 | 1.00 |

Figure 4

| No. CBQ | X | R₁ | R₂ | R₃ |
|---------|---|--------|----|---------|
| 76 | S | 4-Cl | H | H |
| 82 | S | 2,3-diCl | H | H |
| 106 | S | H | H | 10-CH₃ |
| 108 | S | 4-Cl | H | 10-CH₃ |
| 113 | S | 4-Cl | H | 9-OCH₃ |

| Cell Line | Tk6 | Toledo | A431 |
|-----------|-----|--------|------|
| IC₅₀ Dose | 8.6 µM | 50 µM | 23µM |

| CODE | X | R₁ | R₂ | Drug Likeness | MolLogP |
|---|---|---|---|---|---|
| | S | 3-NH₂ | 10-CO-c-C₄H₇ | 1.00 | 5.34 |
| | S | 3-NH(CH₂)₂NH₂ | 10-CO-c-C₄H₇ | 1.19 | 5.72 |
| | S | 2-Cl, 3-NH₂ | 10-CO-c-C₄H₇ | 1.12 | 6.58 |
| ABQ-95 | S | 2-Cl, 3-NH₂ | 10-Me | 0.43 | 6.64 |
| | S | 2-Cl, 3-NHCH₂CH₂N(CH₃)₂ | 10-Me | 0.77 | 7.57 |
| | S | 2-Cl, 3-NH(CH₂)₂NH₂ | 10-Me | -0.05 | 6.87 |
| | S | 4-Cl, 3-NH(CH₂)₂NH₂ | 10-CO-c-C₄H₇ | 1.28 | 6.53 |
| | S | 4-Cl, 3-NH(CH₂)₂NH₂ | 10-CO-c-C₄H₇, 9-F | 1.45 | 6.86 |
| | S | 4-Cl, 3-NH₂ | 10-CO-c-C₄H₇ | 0.97 | 6.09 |
| | S | 2-Cl, 3-NH(CH₂)₂NH₂ | 10-CO-c-C₄H₇ | 1.39 | 6.94 |
| ABQ-91 | S | 3-NH₂ | 10-Me | -0.02 | 5.40 |
| ABQ-2 | S | 3-NH₂ | H | -0.13 | 4.68 |
| | S | 3-NH(CH₂)₂NH₂ | H | 0.32 | 5.23 |
| | S | 3-NHCH₂CH₂N(CH₃)₂ | H | 1.17 | 5.77 |
| | S | H | -O-CH₂CH₂N(CH₃)₂ | 0.56 | 5.97 |
| | S | 3-NH(CH₂)₂N(CH₃)₂ | 10-Me | 0.60 | 6.49 |
| | S | 3-3-NH(CH₂)₂N(CH₃)₂ | 10-OMe | 0.65 | 6.08 |
| | S | 3-NH(CH₂)₂N(CH₃)₂ | 9-OMe | 0.65 | 5.94 |
| | S | 3-NH(CH₂)₂N(CH₃)₂ | 9,10-di-OMe | 0.92 | 5.89 |
| | S | 3-NH(CH₂)₂N(CH₃)₂ | -O-CH₂CH₂N(CH₃)₂ | 0.75 | 6.34 |
| ABQ-38 | NEt | 3-NH₂ | H | -0.56 | 4.47 |
| | NEt | 3-NH(CH₂)₂NH₂ | H | 0.29 | 4.86 |
| | NEt | 3-NH(CH₂)₂N(CH₃)₂ | H | 0.84 | 5.56 |
| | NEt | 3-NH(CH₂)₂NH₂ | 10-CO-c-C₄H₇ | 1.44 | 5.52 |
| | NEt | 3-NH₂ | 10-CO-c-C₄H₇ | 0.93 | 5.13 |
| | NBn | 3-NH(CH₂)₂NH₂ | 10-CO-c-C₄H₇ | 1.14 | 6.77 |

Figure 13

| CODE | X | R₁ | R₂ | Drug Likeness | MolLogP |
|---|---|---|---|---|---|
|  | NBn | 3-NH₂ | 10-CO-c-C₄H₇ | 0.46 | 6.39 |
|  | NAr | 3-NH(CH₂)₂NH₂ | H | 0.32 | 5.60 |
|  | NAr | 3-NH(CH₂)₂N(CH₃)₂ | H | 0.70 | 6.31 |
| ABQ-48 | NBn | 3-NH₂ | H | -0.87 | 5.73 |
|  | NBn | 3-NH(CH₂)₂NH₂ | H | 0.29 | 6.11 |
|  | NBn | 3-NH(CH₂)₂N(CH₃)₂ | H | 0.34 | 6.82 |

Figure 14

| Name | $R_1$ | Molecular Formula | MW (g/mol) |
|---|---|---|---|
| ABQ-48: NSC D-763307 | 3-$NH_2$ | $C_{22}H_{18}ClN_3$ | 359.8514 |
| NBQ-48: NSC D-763303 | 3-$NO_2$ | $C_{22}H_{16}ClN_3O_2$ | 389.8348 |

| Panel | Cell line | % Growth Inhibition | |
|---|---|---|---|
| | | NBQ48 D-763303 | ABQ48 D-763307 |
| Leukemia | K-562 | 53 | 63 |
| | MOLT-4 | 15 | 66 |
| | RPMI-8226 | 48 | 72 |
| | SR | 19 | 77 |
| Non-Small Cell Lung Cancer | A549 | - | 62 |
| | EXVX | 30 | 67 |
| | HOP-92 | - | 71 |
| | NCI-H23 | 47 | 73 |
| Colon Cancer | COLO205 | 13 | 77 |
| | HCC-2998 | 4 | 62 |
| | HCT-116 | 3 | 62 |
| | HT29 | 23 | 55 |
| | KM12 | 8 | 90 |
| CNS Cancer | SF-268 | 55 | 66 |
| | SF539 | 21 | 48 |
| | SNB-19 | 15 | 70 |
| | U251 | 31 | 91 |
| Melanoma | MALME-3M | 51 | 85 |
| | MDA-MB-435 | 7 | 69 |
| | SK-MEL-2 | 15 | 71 |
| | SK-MEL-5 | 76 | 92 |
| Ovarian Cancer | OVCAR-3 | 44 | 80 |
| | OVCAR-4 | 37 | 73 |
| | OVCAR-8 | 34 | 51 |
| | SK-OV-3 | 17 | 65 |
| Renal Cancer | SN12C | 10 | 72 |
| | UO-31 | 7 | 25 |
| Prostate Cancer | PC-3 | 32 | 67 |
| | DU-145 | - | 45 |
| Breast Cancer | MCF-7 | 8 | 51 |
| | MDA-MB-231 | 21 | 16 |
| | HS 578T | 11 | 56 |

Figure 19

| Position | 1H δppm [mult., J (Hz)] | 13C δppm |
|---|---|---|
| 1 | 8.90 [d, 9.3] | 118.08 |
| 2 | 7.43 [dd, 9.2, 2.7] | 121.49 |
| 3 | --- | 148.05 |
| 4 | 7.25 [d, 2.7] | 109.99 |
| 4a | --- | 125.90 |
| 5 | 8.57 [d, 9.6] | 139.57 |
| 6 | 8.28 [d, 9.6] | 108.24 |
| 6a | --- | 141.42 |
| 7 | N | N |
| 7a | --- | 131.97 |
| 8 | 8.13 [dd, 8.4, 1.2] | 112.98 |
| 9 | 7.84 [ddd, 8.2, 7.3, 1.0] | 127.88 |
| 10 | 7.78 [ddd, 8.5, 7.3, 1.3] | 125.62 |
| 11 | 9.06 [d, 8.6] | 116.83 |
| 11a | --- | 127.79 |
| 12 | N | N |
| 12a | --- | 124.74 |
| NH$_2$ | 6.02 | --- |
| CH$_2$ | 6.08 | 46.88 |
| *ipso* | --- | 134.54 |
| *ortho* | 7.38* | 127.03 |
| *meta* | 7.34** | 128.79 |
| *para* | 7.37** | 128.13 |

Figure 21

| Position | $^1$H δppm [mult., $J$ (Hz)] | $^{13}$C δppm |
|---|---|---|
| 1 | 9.44 [d, 9.5] | 119.4 |
| 2 | 8.79 [dd, 9.5, 2.5] | 126.6 |
| 3 | --- | 144.9 |
| 4 | 9.40 [d, 2.5] | 126.3 |
| 4a | --- | 124.3 |
| 5 | 9.06 [d, 9.5] | 140.1 |
| 6 | 8.74 [d, 9.5] | 111.5 |
| 6a | --- | 144.3 |
| 7 | N | N |
| 7a | --- | 132.1 |
| 8 | 8.25 [m] | 113.9 |
| 9 | 7.95* [m] | 128.4 |
| 10 | 7.94* [m] | 127.0 |
| 11 | 9.19 [m] | 117.0 |
| 11a | --- | 128.3 |
| 12 | N | N |
| 12a | --- | 136.7 |
| CH$_2$ | 6.22 [s] | 47.5 |
| ipso | --- | 134.0 |
| ortho | 7.45 [m] | 127.3 |
| meta | 7.41 - 7.26 [m] | 128.9 |
| para | 7.41 - 7.26 [m] | 128.8 |

Figure 22 a. one mol acetic anhydride in cold EtOAc. b, (for 4 or 4a, respectively) 3,4,5- or 2,3,4-trimethoxybenzaldehyde. c. sodium borohydride in dry methanol at rt. d. boiling acetic acid.

METHOD FOR PRODUCING BENZAZOLOQUINOLIUM (BQS) SALTS AND USING THE BIOLOGICAL ACTIVITY OF THE COMPOSITION

RELATED APPLICATIONS

This application is a continuation-in-part of U.S. application Ser. No. 14/857,500, now U.S. Pat. No. 9,889,128, filed on Sep. 17, 2015, which claims the benefit of priority of U.S. provisional application No. 62/051,875 filed Sep. 17, 2014; and also claims the benefit of priority of U.S. provisional application 62/121,157 filed on Feb. 26, 2015.

STATEMENT REGARDING FEDERALLY SPONSORED RESEARCH AND DEVELOPMENT

Parts of this research were supported by grants from the National Center for Research Resources (5P20RR016470-12) and the National Institute of General Medical Science (8 P20 GM103475-12) from the National Institutes of Health.

BACKGROUND OF THE INVENTION

Field of the Invention

The present invention relates to the synthesis, fluorescent properties, and biological activity of benzazolo[3,2-a]quinolinium salts (BQs), more particularly, to a synthesis procedure for producing chloro-substituted (CBQs), amino-substituted (ABQs), and nitro-substituted (NBQs) benzazolo[3,2-a]quinolinium chloride salts that exhibit distinctive biological activity and fluorescent properties.

Discussion of the Background

The scientific community continuously needs to apply cellular markers when studying how cells or subjects respond or behave to a given internal or external stimulus. Some of these stimuli include, but are not limited to, drug treatments, therapies and natural disease processes.

U.S. Pat. No. 4,590,275 to Cox et al. (Cox '275), discloses the preparation of benzazolo[3,2-a]quinolinium chloride salts (BQs) which show cytotoxic, antitumor and antiviral activity. However Cox '275 fails to disclose the synthesis of amino-substituted (ABQs) and chloro-substituted (CBQs) benzazolo[3,2-a]quinolinium compounds, wherein said ABQs and CBQs possess fluorescent properties applicable in the identification of cellular organelles and biological activities applicable for therapeutic applications. The fluorescent property assists the user to identify cellular organelles making the compounds excellent markers for research, diagnostic or treatment. Some of the biological activities include, but are not limited to, cellular toxicity, mitochondria damage and apoptosis induction on tumor cell lines in culture.

Also Cox '275 discloses different methods for the synthesis of several compounds; however the disclosed methods do not limit the excitation by irradiation of the compounds in order to avoid unwanted reactions resulting in unwanted characteristics and properties. Further in Cox '275 the BQs were isolated as the perchlorate salt through its precipitation by addition of an aqueous perchloric acid or a saturated sodium perchlorate solution avoiding isolating the pure BQs.

Also, the search for novel, active compounds against cancer has led to the study of natural products or their derivatives. Many such compounds have shown activity against cancer cells. Among these naturally derived substances are ellipticine (from *Ochrosia*), berberine (from *Berberis*) and etoposide (from *Podophyllum*). Ellipticine and its analogs have been widely studied and deemed active against a variety of cancer types with limited side effects, as mentioned in the document titled "Ellipticine cytotoxicity to cancer cell lines—a comparative study", *Interdisciplinary toxicology*, 2011, 4(2), 98-105 and "DNA adduct formation by the anticancer drug ellipticine in human leukemia HL-60 and CCRF-CEM cells", *Cancer letters*, 2007, 252(2), 270-279 (both documents included by reference).

SUMMARY OF THE INVENTION

The present invention overcomes the limitations of the synthesized benzazolo[3,2-a]quinolinium chloride salts as presented by Cox '275 et al. and discloses a synthesis procedure that increases the biological activity and greater selectivity toward tumor cells providing the autofluoresce in cell cultures, inducing cytotoxity through apoptosis, binding to cellular organelles and caspaces activation on human tumor (abnormal) or normal cells in culture.

First, the present invention discloses several compounds, such as amino-substituted benzazolo[3,2-a]quinolinium showing (1) DNA fragmentation; (2) cell cycle disruption; (3) cellular toxicity; and (4) generation of reactive oxygen species (ROS). Also the compound has shown auto-fluorescent properties in contact with cells. These fluorescent properties allow a clear indication of the interaction with cellular organelles serving as a fluorescence marker in research or as a therapeutic marker or a diagnostic marker in clinical studies. It could be applied to monitor the presence and concentrations of microorganisms in the environment since they also possess cellular organelles to which these fluorescent compounds can bind. Further the ABQs display increased selectivity against cancer cells as compared to NBQs.

Second, the present invention discloses the synthesis of chloro-substituted and amino-substituted benzothiazolo[3,2-a]quinolinium salts causing cell death via an apoptosis mechanism, interaction with macro organelles such as mitochondria and DNA, activation of caspases 3 and 7, and the formation of 8-2-dG adducts upon bioreduction in the presence of XO/HX.

Third the present invention discloses an improved procedure for the synthesis of benzothiazolo[3,2-a]quinolinium salts (BQs).

Therefore one of the objectives of the present invention is to provide a compound showing DNA fragmentation, cell cycle disruption, cellular toxicity, generation of reactive oxygen species, and autofluorescence.

Another object of the invention is to provide a synthesized nitro-substituted, amino-substituted, and chloro-substituted benzothiazolo[3,2-a]quinolinium salts (BQs) causing cell death via an apoptosis mechanism, interaction with macro organelles such as mitochondria and DNA, activation of caspases 3 and 7, and the formation of 8-2-dG adducts upon bioreduction in the presence of XO/HX.

Another objective of the invention is to provide a synthesized nitro-substituted amino-substituted, and chloro-substituted benzothiazolo[3,2-a]quinolinium salts that allows the identification of tumor cells.

Another objective of the invention is to provide a new improved method for the synthesis of BQs which is more compatible with the biological systems.

Another objective of the invention is to provide a synthesis method of BQs that avoids unwanted reactions.

Another objective of the invention is to provide a synthesis method of BQs that improves performance of the compounds.

Another objective of the present invention is to provide a compound suitable as an anti-cancer therapeutic agent, bacterial marker, and antibacterial.

Another objective of the present invention is to determine the metabolic activity of cells or tissues under low or no oxygen content (hypoxic environment). The reagent is a non-fluorescent compound that can be transformed into a fluorescent metabolite by hypoxic cells that are alive and metabolically active.

Another objective is the chemical synthesis, characterization and anti-cancer activities, of 7-benzyl-3-aminobenzimidazo[3,2-a]quinolinium chloride (ABQ-48: NSC D-763307) and the corresponding 7-benzyl-3-nitrobenzimidazo[3,2-a]quinolinium chloride (NBQ 48: NSC D-763303), as determined by the National Cancer Institute (NCI) 60 human tumor cell line screen. Although we have synthesized and tested several BQS analogues (as shown in the following documents, here included by reference, "Novel Nitrobenzazolo[3,2-a]quinolinium Salts Induce Cell Death through a Mechanism Involving DNA Damage, Cell Cycle Changes, and Mitochondrial Permeabilization"; "Effects of the anti-tumor drugs 3-nitrobenzothiazolo[3,2-a]quinolinium and fagaronine on nucleic acid and protein synthesis"; "Synthesis and biological activity of benzothiazolo- and benzoxazolo[3,2-a]quinolinium salts. Journal of medicinal chemistry"; and "Method for producing benzazoloquinolinium salts (bqs), using the composition as cellular markers, and using the biological activity of the composition, U.S. US 20120129882) we decided to disclose the data obtained for these two closely structurally related analogues where the only structural variation is the incorporation, at position 3 of ring A, of a nitro vs. an amino substituent in NBQ-48 and ABQ-48, respectively. These compounds belong to a novel series of unnatural alkaloids known as benzazolo[3,2-a]quinolinium salts (BQS) and are structurally related to ellipticine. BQS compounds are characterized by planar heterocyclic structure, a quaternized nitrogen, a fused benzothiazole nucleus and an amino or nitro substituent at the 3-position in ring A (FIG. 1). Our previous work on the nitro-substituted members (NBQ) of this family has demonstrated cytotoxic activity on cancer cell lines such as epidermoid carcinoma, Ehrlich ascites in mice and P-388 leukemia. Additional studies have demonstrated the capacity of the NBQ compounds to generate DNA adducts.

Another objective is to disclose the varied cell toxicity effects and biological activities of derivatives of 3-nitro-7-benzyl- and 3-amino-7-benzylbenzimidazo[3,2-a]quinolinium chlorides (NBQ-48 and ABQ-48, respectively), with methoxy substituents at the N-7-benzyl ring. This substitution leads to two different series, namely, 3-nitro-7-(3,4,5-trimethoxybenzyl)- and 3-amino-7-(2,3,4-trimethoxybenzyl)benzimidazo[3,2-a]quinoliniun chlorides derivatives.

The invention itself, both as to its configuration and its mode of operation will be best understood, and additional objects and advantages thereof will become apparent, by the following detailed description of a preferred embodiment taken in conjunction with the accompanying drawing.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings, which are incorporated herein, constitute part of the specifications and illustrate the preferred embodiment of the invention.

FIG. 3 shows fluorescence characterization of representative ABQ48.

FIG. 4 shows Fluorescence data of CBQs in water solution.

FIG. 13 through FIG. 14 represent ABQs Drug-likeness analysis.

FIG. 19 shows NCI 60 screening results. Cell culture panel and growth inhibition percentage.

FIG. 21 shows proton and Carbon-13 NMR assignments for ABQ-48.

FIG. 22 shows proton and Carbon-13 NMR assignments for NBQ-48.

FIG. 37 shows the synthesis of benzimidazoles 6 and 6a.

DESCRIPTION OF THE PREFERRED EMBODIMENT

Figures 1, 2:
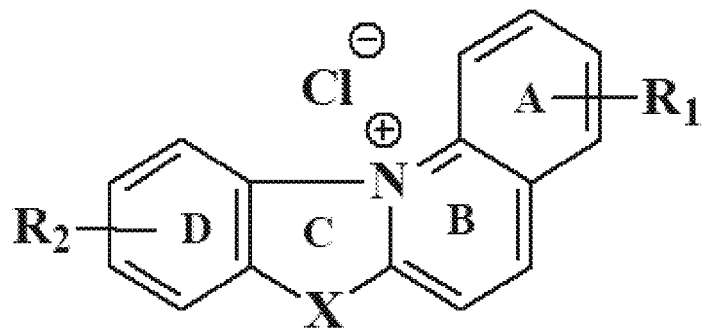
FIG. 1 shows the structure of a preferred embodiment of the present invention.
FIG. 2 shows list of developed ABQs.

FIG. 1 shows a general structure of the synthesized NBQs and ABQs. The present invention is particularly directed to the synthesis and biological activity of ABQs as shown in FIG. 2. The synthetic sequence is disclosed in patent application Ser. No. 12/416,174, included here by reference.

The particular methodology or method comprises several measurements and apparatus used in order to perform the synthesis of the compounds. The BQs, NBQs and ABQs, were synthesized using several methods as disclosed in patent application Ser. No. 12/416,174 herein included by reference.

The synthesis of benzazolo[3,2-a]quinolinium chlorides are performed using at least four different methods, as disclosed in patent application Ser. No. 12/416,174 herein included by reference.

Further a green procedure for the synthesis of benzazolo [3,2-a]quinolinium salts (Method 5) was developed. The photochemical cyclization and work-up procedure for the synthesis of benzazolo[3,2-a]quinolinium salts was described in the first application (Ser. No. 12/416,174) as Methods 1, 2, 3, or 4. New Method 5 is partially similar as described before, except that the corresponding (E)-2-(2-chlorostyryl)benzazole was dissolved in 150-250 mL of a 2:2:1 heptane (or octane):dioxane:bromobenzene mixture. The elimination of benzene as a solvent constitutes an environmentally friendlier or green chemical procedure. The following is a representative example of the use of Method 5.

Representative Example to Validate the Modified Method—

7-benzyl-3-nitrobenzimidazolo[3,2-a]quinolinium chloride (NBQ-48).

Photochemically induced cyclization of (E)-7-benzyl-2-(2-chloro-3-nitrostyryl)benzimidazole as described in Method 5 produced the title compound, in 70% yield, identical in all respects to that of a sample obtained using Method 1 of patent application Ser. No. 12/416,174.

Experimental Procedures, Physical Properties, and Chemical Characterization of New ABQs.

1. 7-Benzyl-3-aminobenzimidazo[3,2-a]quinolinium chloride (ABQ-48). (E)-7-benzyl-2-(2-chloro-3-aminostyryl) benzimidazole was photocyclized using the new procedure described in to give the title compound as a bright yellow solid. UV-vis (PBS 7.4 Buffer) λmax/nm (ε $M^{-1}cm^{-1}$): 259 (2.94×$10^4$), 330 (1.29×$10^4$), 342 (1.18× $10^4$), 371 (4.54×$10^3$). $^1$H NMR (DMSO-$d_6$, 400 MHz) δ 9.04 (d, J=8.40 Hz, 1H), 8.87 (d, J=9.60 Hz, 1H), 8.54 (d, J=9.60 Hz, 1H), 8.27 (d, J=9.60 Hz, 1H), 8.12 (d, J=7.60 Hz, 1H), 7.79 (t, J=7.70 Hz, 1H), 7.77 (t, J=7.60 Hz, 1H), 7.29 (dd, J=9.20, 2.4 Hz, 1H), 7.33 (m, 5H), 7.24 (d, J=2.4 Hz, 1H), 6.08 (2H), 6.03 (2H). HRMS (ESI): m/z Calcd. for $C_{22}H_{18}N_3$ (without the chloride counter ion) 324.14952. Found: 324.14812 (Δ −4.33 ppm).

2. 10-Methyl-3-aminobenzothiazolo[3,2-a]quinolinium chloride (ABQ-91). (E)-5-methyl-2-(2-chloro-5-aminostyryl)benzothiazole was photocyclized using the new procedure to produce the title compound as a yellow solid. $^1$H NMR (DMSO-$d_6$, 400 MHz) δ 9.13 (d, J=9.60 Hz, 1H), 8.99 (s, 1H), 8.63 (d, J=9.20 Hz), 8.55 (d, J=9.20 Hz), 8.46 (d, J=8.40), 7.75 (d, J=8.9 Hz), 7.52 (d, 8, 0 H, 1H), 7.28 (s, 1H), 2.70 (s, 3H). HRMS (ESI): m/z Calcd. for $C_{16}H_{13}N_2S$ (without the chloride counter ion) 265.07940. Found: 265.07838 (Δ −3.84 ppm). UV-vis 3. 3-Aminobenzothiazolo[3,2-a]quinolinium chloride (ABQ-2). (E)-(2-chloro-5-aminostyryl)benzothiazole was photocyclized using the new procedure to produce the title compound as a yellow solid. $^1$H NMR (DMSO-$d_6$, 400 MHz) δ 9.20 (d, J=8.00 JH, 1H), 9.08 (d, J=9.69 Hz, 1H), 8.67 (d, J=8.80 Hz, 1H), 8.61 (m, 2H), 7.90 (m, 2H), 7.53 (d, J=9.60, 1H), 7.30 (d, J=2 Hz, 1H). HRMS (ESI): m/z Calcd. for $C_{15}H_{11}N_2S$ (without the chloride counter ion) 251.06375. Found: 251.06279 (Δ −3.91 ppm).

4. 9-Methoxy-3-aminobenzothiazolo[3,2-a]quinolinium chloride (ABQ-25). (E)-6-methoxy-(2-chloro-5-aminostyryl)benzothiazole was photocyclized to give the title compound as a yellow solid. HRMS (ESI): m/z Calcd. for $C_{16}H_{13}N_2OS$ (without the chloride counter ion) 281.07410. Found: 281.07431 (Δ −0.75 ppm).

5. Other ABQS are
   a. 7-Benzyl-3-aminobenzimidazo[3,2-a]quinolinium chloride (ABQ-48);
   b. 3-Aminobenzothiazolo[3,2-a]quinolinium chloride (ABQ-2);
   c. 9-Methoxy-3-aminobenzothiazolo[3,2-a]quinolinium chloride (25);
   d. 10-Methyl-3-aminobenzothiazolo[3,2-a]quinolinium chloride (ABQ-91);
   e. 10-Methoxy-3-aminobenzothiazolo[3,2-a]quinolinium chloride (ABQ-97);
   f. 7-(Methyl)-3-aminobenzimidazo[3,2-a]quinolinium chloride (ABQ-47);
   g. 7-(Isopropyl)-3-aminobenzimidazo[3,2-a]quinolinium chloride (ABQ-49);
   h. 7-(1-Butyl)-3-aminobenzimidazo[3,2-a]quinolinium chloride (ABQ-50);
   i. 7-[(E)-1-Propenyl)]-3-aminobenzimidazo[3,2-a]quinolinium chloride (ABQ-59);
   j. 7-Cyclopentyl-3-aminobenzimidazo[3,2-a]quinolinium chloride (ABQ-60);
   k. 3-Aminonaphtho[1',2':4,5]benzothiazolo[3,2-a]quinolinium chloride (ABQ-74);
   l. 10-Methoxy-4-chloro-3-aminobenzothiazolo[3,2-a]quinolinium chloride (ABQ-121);
   m. 9-Methoxy-2-aminobenzothiazolo[3,2-a]quinolinium chloride (ABQ-122);

n. 8,9-Dimetoxy-3-aminobenzothiazolo[3,2-a]quinolinium chloride (ABQ-84).

Synthesis and Characterization of Fluorescent Chloro-Substituted benzazolo[3,2-a]quinolinium Chloride Salts (CBQs).

6. 4-Chlorobenzothiazolo[3,2-a]quinolinium chloride (CBQ-76). Method 1. Following the procedure for synthesis of benzazolo[3,2-a]quinolinium chlorides described in patent application Ser. No. 12/416,174, (E)-2-(2,6-dichlorostyryl) benzothiazole (0.6 g, 1.96 mmol) was photocyclized to afford 0.30 g (50%) of CBQ-76 as a yellow solid: mp 238° C. (dec.); $^1$H NMR (500.13 MHz, DMSO-$_{d6}$): δ ppm 9.35 (d, 1H, J=8.7 Hz), 9.25 (d, 1H, J=8.5 Hz), 9.15 (1H, d, J=9.8 Hz), 8.99 (1H, d, J=9.4 Hz), 8.72 (1H, dd, J=7.9, 1.4 Hz), 8.25 (1H, dd, J=7.5, 0.7 Hz), 8.20 (1H, t, J=8.3 Hz), 8.00 (2H, m); $^{13}$C NMR (125.77 MHz, DMSO-$_{d6}$): δ ppm 160.35, 138.97, 137.88, 135.52, 133.83, 133.22, 129.96, 129.63, 129.53, 129.27, 125.57, 124.90, 120.99, 120.52, 118.85; UV-vis (EtOH, 95%), $\lambda_{max}$/nm (ε): 380 (10444), 364 (10905), 259 (16538), 225 sh (12273) and 201 (23193); Anal. calcd for $C_{15}H_9NSCl_2 \cdot 2.5H_2O$: C, 51.47; H, 4.03; N, 4.00%. Found C, 50.98; H, 3.54; N, 4.34%.

7. 3,4-Dichlorobenzothiazolo[3,2-a]quinolinium chloride (CBQ-82). Method 1. Following the procedure for synthesis of benzazolo[3,2-a]quinolinium chlorides described in patent application Ser. No. 12/416,174, (E)-2-(2,3,6-trichlorostyryl)benzothiazole (1p) (0.26 g 0.66 mmol) was photocyclized to afford 0.114 g (44%) of CBQ-82 as a yellow solid: mp 250-260° C. (dec.); $^1$H NMR (300.15 MHz, DMSO-$_{d6}$): δ ppm 9.36 and 8.38 (AB, 2H, J=9.6 Hz), 9.21 (dd, 1H, J=9.9, 1.2 Hz), 9.18 and 9.06 (AB, 2H, J=9.6 Hz), 8.74 (dd, 1H, J=7.8, 1.8 Hz), 8.03 (m, 2H); $^{13}$C NMR (75 MHz, DMSO-$_{d6}$): 160.1, 138.8, 136.4, 135.5, 133.6, 132.6, 131.0, 130.0, 129.6, 129.4, 126.4, 125.6, 122.0, 120.4, 120.0; UV-vis (95% EtOH) $\lambda_{max}$/nm (ε) 382 (7402), 366 (8676), 263 (17038), 237 sh (10992) and 201 (22618); Anal. calcd for $C_{15}H_8NSCl_3 \cdot 2H_2O$: C, 44.23; H, 2.97; N, 3.44%. Found C, 43.89; H, 2.68; N, 3.32%.

8. 10-Methylbenzothiazolo[3,2-a]quinolinium chloride (CBQ-106). Method 3. Following the procedure for synthesis of benzazolo[3,2-a]quinolinium chlorides described in patent application Ser. No. 12/416,174, (E)-5-methyl-2-(2-chloro-styryl)benzothiazole (1b) (0.65 g, 2.27 mmol) was photocyclized under argon atmosphere to afford 0.35 g (54%) of CBQ-106 as an off-white solid: mp>200° C. (dec); $^1$H NMR (300.15 MHz, DMSO-$_{d6}$): δ ppm 9.43 (d, 1H, J=8.7 Hz), 9.09 (s, 1H), 8.94 and 8.81 (AB, 2H, J=9.0 Hz), 8.53 (d, 1H, J=8.1 Hz), 8.51 (dd, 1H, J=8.6, 1.5 Hz), 8.24 (td, 1H, J=8.1, 1.7 Hz), 8.06 (t, 1H, J=7.7 Hz), 7.81 (d, 1H, J=8.7 Hz), 2.72 (s, 3H, —CH$_3$); $^{13}$C NMR (75 MHz, DMSO-$_{d6}$): δ ppm 159.7, 140.1, 139.8, 139.2, 136.7, 133.7, 130.9, 130.4, 129.0, 127.1, 126.6, 124.8, 119.9, 119.4, 119.3, 21.5; UV-vis (H$_2$O) $\lambda_{max}$/nm (ε): 379 (11622), 365 (11842), 348 sh (8755), 253 (18598), 231 sh (17118) and 223 (17816).

9. 4-Chloro-10-methylbenzothiazolo[3,2-a]quinolinium chloride (CBQ-108). Method 3. Following the procedure for synthesis of benzazolo[3,2-a]quinolinium chlorides described in patent application Ser. No. 12/416,174, (E)-4-methyl-2-(2,6-dichlorostyryl)benzothiazole (1r) (0.57 g, 1.75 mmol) was photocyclized under argon atmosphere and to afford 0.37 g (65%) of CBQ-108 as a yellow solid: mp 250° C. (dec); $^1$H NMR (500 MHz, DMSO-$_{d6}$): δ ppm 9.40 (d, 1H, J=8.6 Hz), 9.11 and 8.95 (2H, AB, J=9.4 Hz), 9.04 (1H, s), 8.57 (1H, d, J=8.3 Hz), 8.24 (1H, d, J=7.4 Hz), 8.19 (1H, t, J=8.5 Hz), 7.83 (1H, d, J=8.4 Hz), 2.71 (3H, s, —CH$_3$); $^{13}$C NMR (125.77 MHz, DMSO-$_{d6}$): δ ppm 160.33, 140.36, 139.29, 137.85, 135.13, 133.73, 133.11, 130.66, 129.57, 127.05, 124.99, 124.87, 121.02, 120.03, 119.02, 21.50; Anal. calcd for $C_{16}H_{11}NSCl_2 \cdot 1.5H_2O$: C, 55.54; H, 4.08; N, 4.05%. Found C, 55.80; H, 3.53; N, 4.36%.

10. 4-Chloro-9-methoxybenzothiazolo[3,2-a]quinolinium chloride (CBQ-113). Method 3. Following the procedure for synthesis of benzazolo[3,2-a]quinolinium chlorides described in patent application Ser. No. 12/416,174, (E)-6-methoxy-2-(2,6-dichlorostyryl)benzothiazole (1q) (0.18 g, 0.54 mmol) was photocyclized to afford 0.12 g (67%) of CBQ-113 as a yellow solid: mp 250-260° C. (dec.); $^1$H NMR (300.15 MHz, DMSO-$_{d6}$): δ ppm 9.28 (d, 1H, J=8.4 Hz), 9.14 (d, 1H, J=9.9 Hz), 9.08 and 8.94 (AB, 2H, J=9.3 Hz), 8.30 (d, 1H, J=2.7 Hz), 8.20 (m, 2H), 7.55 (dd, 1H, J=9.6, 2.7 Hz), 3.99 (3H, s, —OCH$_3$); $^{13}$C NMR (75 MHz, DMSO-$_{d6}$): δ ppm 159.33, 158.78, 137.44, 134.31, 133.64, 133.09, 132.90, 132.30, 129.52, 124.88, 121.50, 120.87, 118.58, 118.20, 107.55, 56.34; Anal. calcd for $C_{16}H_{11}Cl_2NOS \cdot 1.5H_2O$: C, 53.08; H, 3.90; N, 3.87%. Found C, 53.47; H, 3.93; N, 3.75%.

The inclusion of the chloro-substituents, amino-substituents, and nitro-substituents in ring A to the synthesis of (E)-2-styrlbenzazole and benzazolo[3,2-a]quinolinium chlorides (BQs) results in ABQs and NBQs providing several properties, more particularly exhibiting an increment in the biological activity. For example FIG. 3 provides the characterization of the representative the ABQ48.

Figures 5, 6:
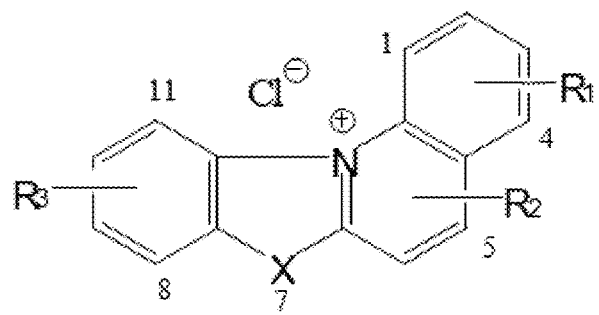
FIG. 5 shows a list of developed fluorescent chloro-substituted benzazolo[3,2-a]quinolinium salts.
FIG. 6 shows average $IC_{50}$ Doses of ABQ48.
Figure 7:
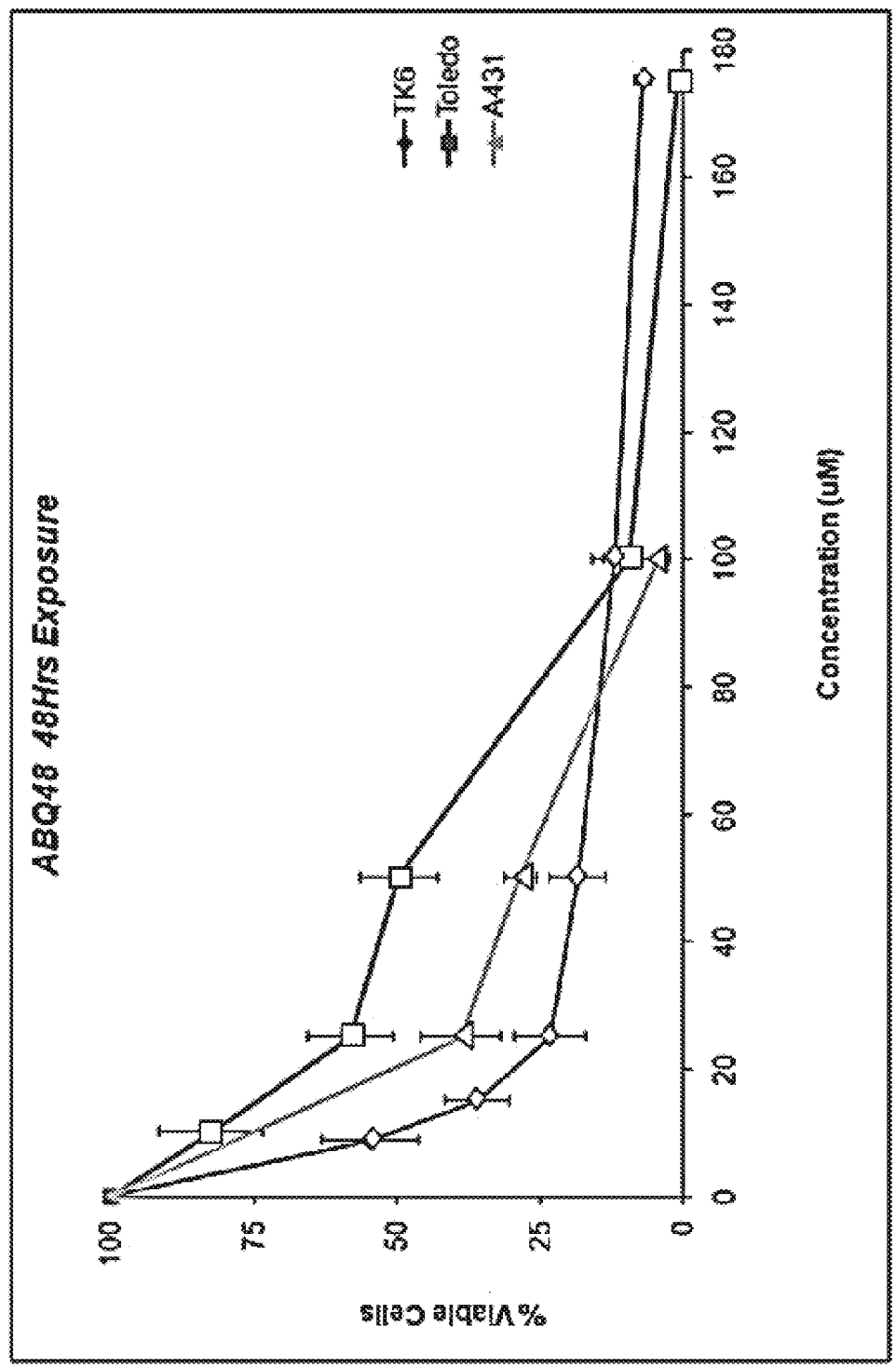
FIG. 7 shows 48 hour dose-response curve for ABQ48 on Tk6, Toledo, and A431 cell lines.

FIGS. 4 and 5 show the fluorescent chloro-substituted benzazolo[3,2-a]quinolinium salts. This new series of halogen substituted benzazolo[3,2-a]quinolinium salts; without nitro or amino substituents display relatively high fluorescence intensity in aqueous solution (see FIG. 4) thus making them potentially useful cellular markers similar to ABQs. For example 4-chloro-10-methylbenzothiazolo[3,2-a]quinolinium chloride (CBQ-108) displays good florescence intensity and cytotoxicity activity against A-431 cell line (IC$_{50}$ 3.7 μM).

Further FIG. 6 to FIG. 12 discloses the biological activity of ABQ48. The biological activities identified are:

Bioactivity 1: Cellular Toxicity of ABQ48 on A431, Toledo, and Tk6 Cell Lines.

The presented data summarize the performed assays aimed to determine the cellular toxicity effects of ABQ 48, an amino substituted alkaloid with fluorescent properties in mammalian cell lines in culture: A431 (epitheloid carcinoma cells), Toledo (lymphoma cells), both abnormal cells, and Tk6 (normal lymphoblasts). The evaluated biological activities with ABQ48 included: cell viability (IC$_{50}$), mitochondrial membrane potential; DNA fragmentation and change in the cell cycle on one or more of the above mentioned cell lines.

Materials and Methods

Cell Cultures—

The three cell lines A431 epitheloid carcinoma cells (ATCC CRL-1555), the human TK-6 lymphoblasts cells (ATCC CRL-8015) and Toledo lymphoma (CRL-2631 respectively) were obtained from American Type Culture Collection (ATCC, Manassas, Va.) and cultured on RPMI 1640 (ATCC) cell culture media with 10% fetal bovine serum (ATCC). Cell cultures were maintained in a cell culture incubator at 37° C. and 5% CO$_2$.

Reagents—Characterizations and purity confirmation of the experimental compounds were determined with Waters, Electrospray Mass Spectrometer (ESI-MS) Quattro Micro mass spectrometer (Milford, Mass.). ABQ 48 Stock Solution of 3 mM was prepared using mass spectrometry grade water (Sigma, St. Louis Mo.) under sterile conditions The ESI-MS conditions used were as follow: drying gas, $N_2$; flow rate, 200 L/h; capillary voltage, 3.0 kV; cone voltage, 16 V; extractor, 25 V; source temperature, 120° C.; and desolvation temperature, 100° C.

Methods—Cultures were exposed for 48 hours to ABQ 48 at doses from 10 µM to 180 µM. Cells were harvested counted and assessed for cell viability implementing the Trypan Blue exclusion method using the Countess™ automated cell counter (Invitrogen Corp. Carlsbad, Calif.). The percentage of viable cells was calculated and graphed using Excel (Microsoft Corp. Redmond, Wash.). The mitochondrial membrane permeability assays was determined applying the Nucleocounter 3000, JC-1 assay. DNA fragmentation and cell cycle alterations were analyzed also through the Nucleocounter 3000 instrument.

Results and Discussion

Reduction in the cell viability of the three cell lines after 24 and 48 hours treatments was observed. Higher susceptibility was observed by Tk6 lymphoblasts with an average $IC_{50}$ of 8.6 µM in contrast to Toledo cells with an $IC_{50}$ of 50 µM which were the least susceptible cultures to the drug. The $IC_{50}$ of the A431 (epitheloid carcinoma) cells was 23 µM (FIG. 6) which is comparable to other previously studied BQs compounds of this family (Vivas—Mejia, 1998; Arroyo and Zayas, 2007; unpublished data). FIG. 1 presents the comparative dose response curve and $IC_{50}$ for ABQ 48 in the three cell lines. Mitochondrial membrane permeability, DNA fragmentation and cell cycle alteration was also observed in the three cell lines.

Bioactivity 2: Time Dependent Uptake and Retention of ABQ48 on Cells Up to 24 Hours This assay aims to determine the uptake and retention of the fluorescence ABQ48 on three cell lines as a function of time. The cell lines used were A431 epitheloid carcinoma, Toledo lymphoma and Tk6 normal lymphoblast.

Materials and Methods

Cell Cultures—The three cell lines A431 epitheloid carcinoma cells (ATCC CRL-1555), the human TK-6 lymphoblasts cells (ATCC CRL-8015) and Toledo lymphoma (CRL-2631 respectively) were obtained from American Type Culture Collection (ATCC, Manassas, Va.) and cultured on RPMI 1640 (ATCC) cell culture media with 10% fetal bovine serum (ATCC). Cell cultures were maintained in a cell culture incubator at 37° C. and 5% $CO_2$.

Reagents—Characterization and purity determination of the experimental compound was determined with a Waters, Quattro Micro mass spectrometer (Milford, Mass.). ABQ 48 (FIG. 9) Stock Solution of 3 mM was prepared using mass spectrometry grade water (Sigma, St. Louis Mo.) under sterile conditions. The ESI-MS conditions used were as follow: drying gas, $N_2$; flow rate, 200 L/h; capillary voltage, 3.0 kV; cone voltage, 16 V; extractor, 25 V; source temperature, 120° C.; and desolvation temperature, 100° C.

Methods—A431 epitheloid carcinoma, Toledo lymphoma and Tk6 normal lymphoblast cultures were exposed to ABQ 48 and incubated at 37° C. and 5% $CO_2$ for 0, 1, 4 and 18, hours at their $IC_{90}$ dose (90 µM, 100 µM, and 135 µM respectively). A non-exposed negative control (analytical grade water) for each determined time point was also included. Cells were then washed twice with PBS (Sigma, St. Louis Mo.) and their fluorescence in standard units (FSU) measured using a Modulus fluorometer (Promega, Sunnyvale, Calif.). Triplicate measures were obtained from each sample. Values were then averaged and background corrected using the negative control values. A one way ANOVA with fixed effects was performed; in case significant differences were found in ANOVA, a Post Hoc Test Tukey Honestly Significant Difference (HSD) was also performed using SPSS software (IBM, Armonk, N.Y.).

Results and Discussion

Figure 8:
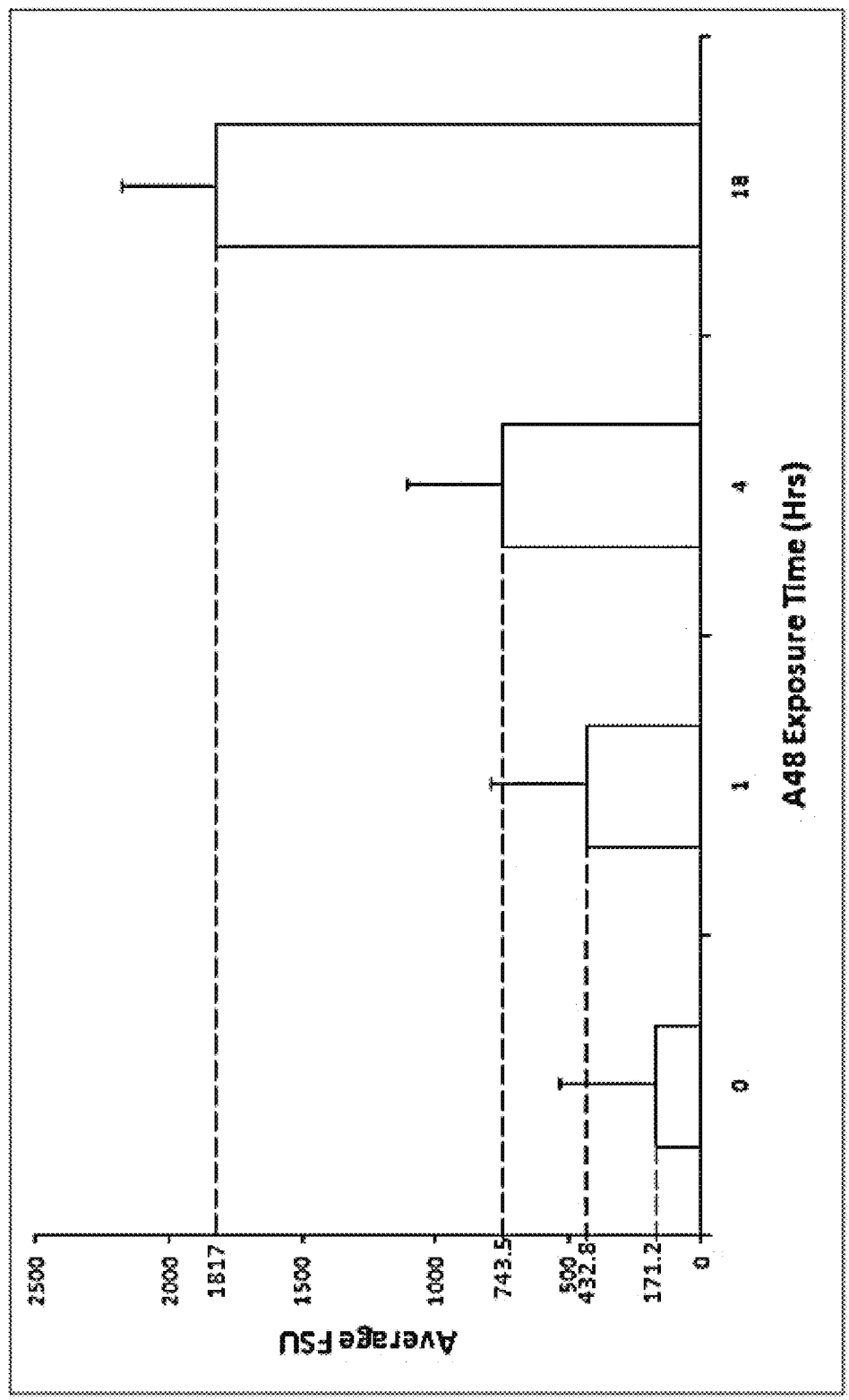
FIG. 8 shows fluorescence uptake of ABQ48 by Tk6 as a function of time (0 to 18 hours).
Figure 9:
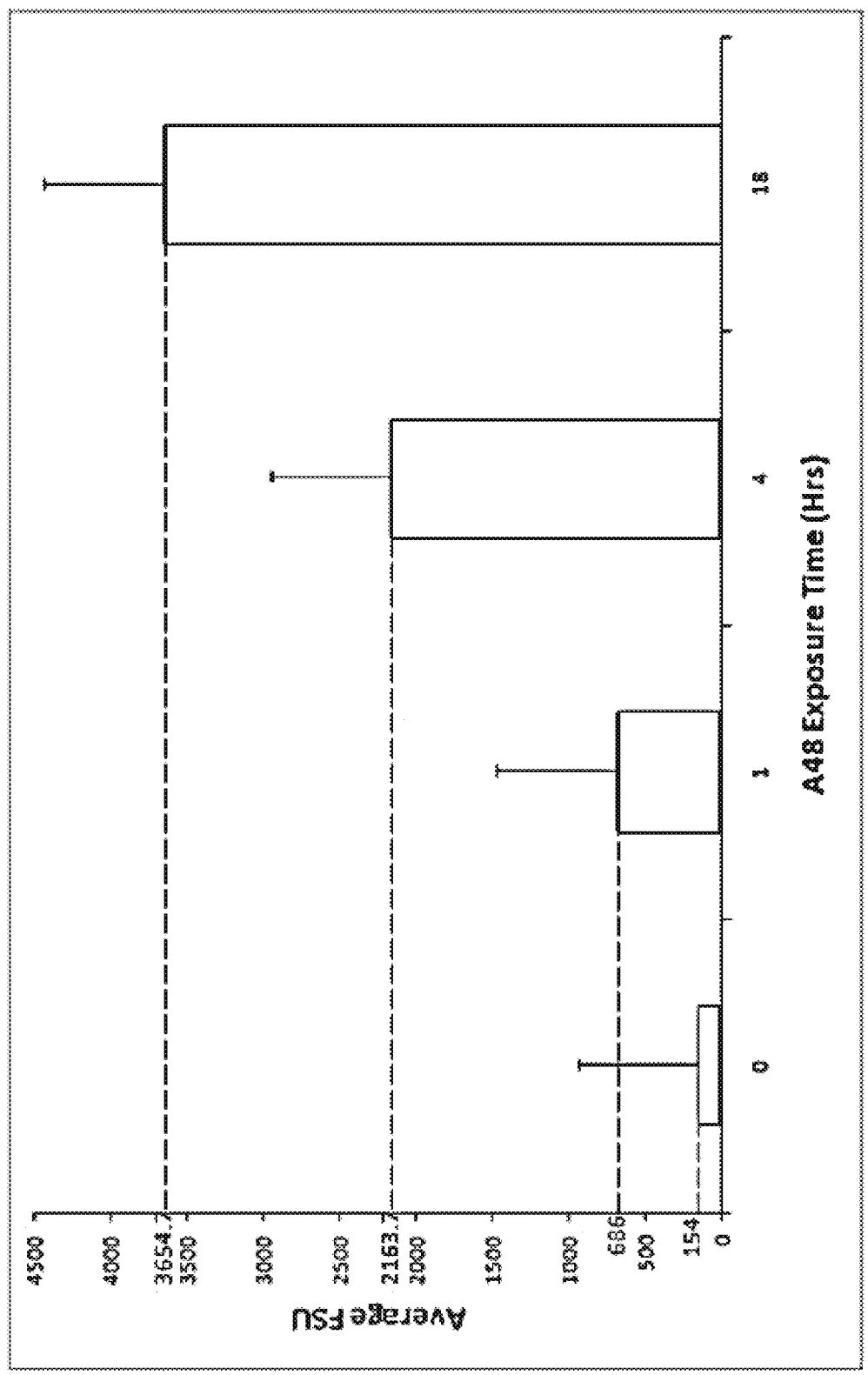
FIG. 9 shows fluorescence uptake of ABQ48 by Toledo as a function of time (0 to 18 hours).
Figure 10:
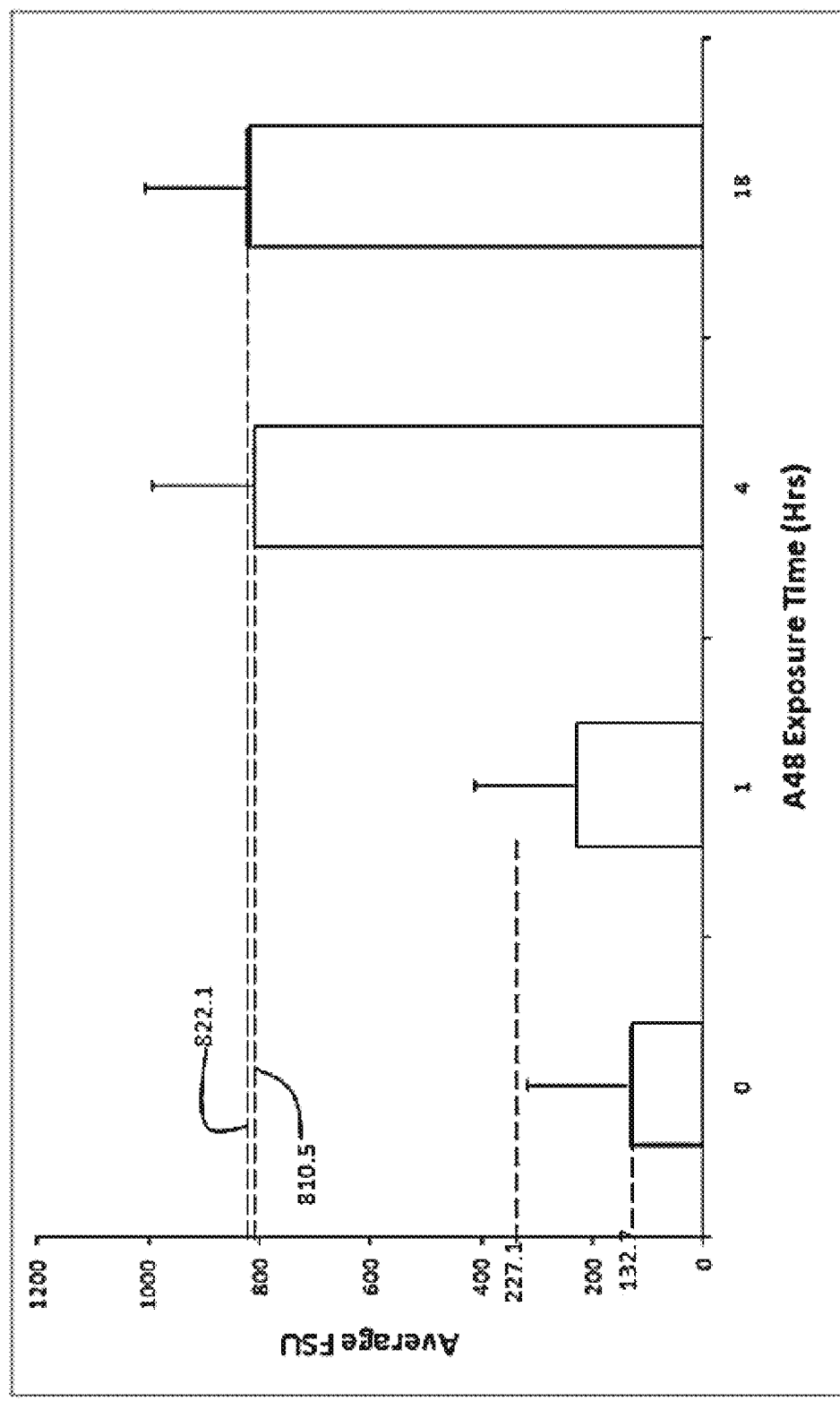
FIG. 10 shows fluorescence uptake of ABQ48 by A431 as a function of time (0 to 18 hours).

The time dependent drug uptake assay clearly demonstrated an increment in the fluorescent emission of cells from three different cell lines (A431, Toledo, and TK6) when treated with ABQ48 for 0 hour, 1 hour, 4 hours, and 18 hours indicating the uptake and retention of A48 in the cells. Results were measured in Fluorescence Standard Units (FSU) versus time of exposure (FIG. 8-10).

Bioactivity 3. DNA Fragmentation—Fragmentation of DNA as a marker for apoptosis is a commonly used assay. Analysis was performed applying the Nucleo counter NC3000 DNA fragmentation assay. Determination of the degree of DNA fragmentation is based on the retention of DAPI, a nucleic acid staining reagent. As described previously TK-6, and Toledo cells were kept in culture at the specified conditions. Cells where then treated with the tested compounds as previously described for 48 hours, after which nutritional media removed, cells harvested, fixed with 70% ethanol, incubated and stained with 1 µg/ml DAPI according to manufacturer's specifications for image analysis measuring DAPI intensity.

Results and Discussion

Figure 11:
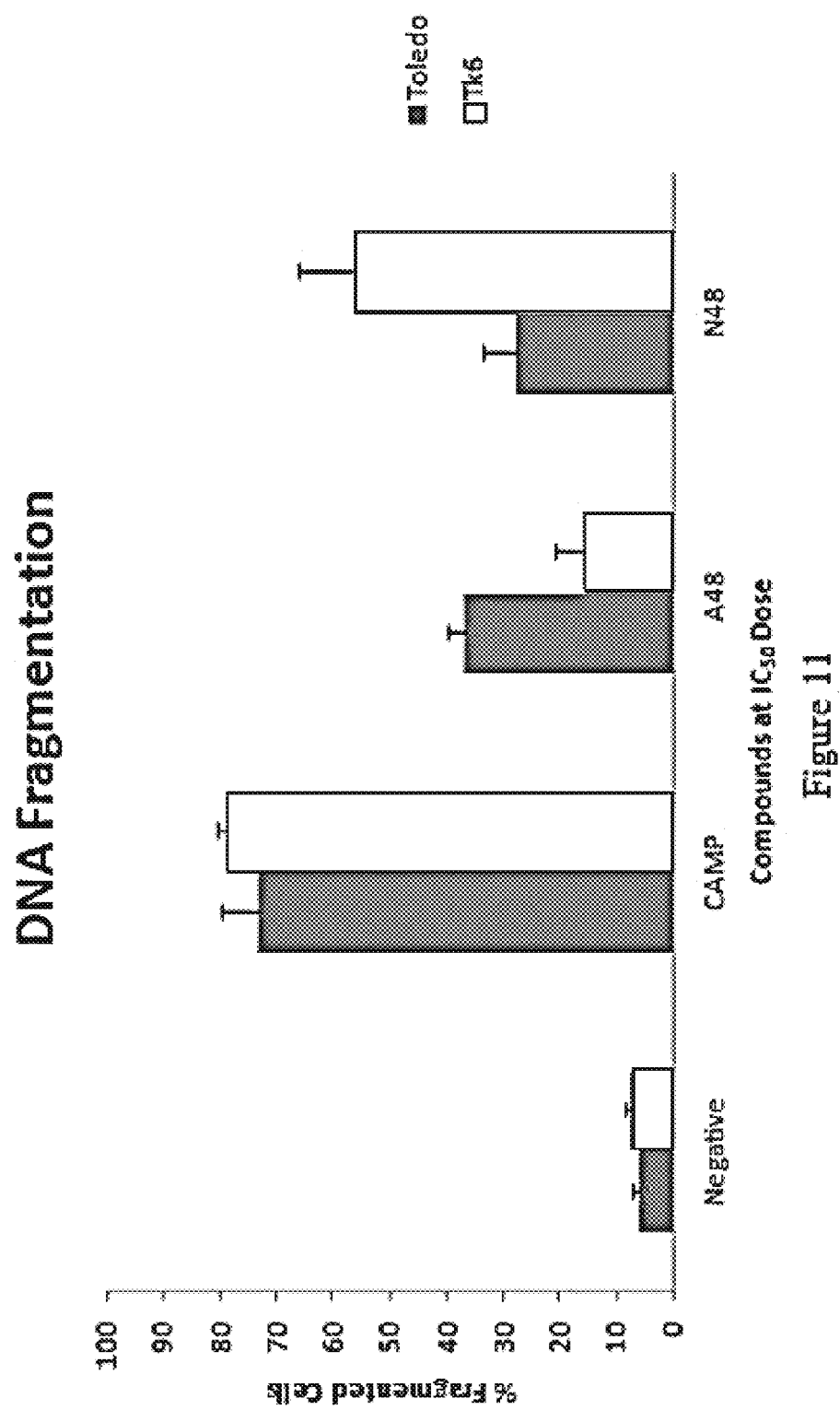
FIG. 11 shows DNA Fragmentation analysis of Toledo and TK6 cells treated with ABQ48 and NBQ48 for 48 hours.

As presented in FIG. 11 cells treated with ABQ48 and NBQ48 presented DNA fragmentation at different levels depending on the cell type, but higher than the negative control population.

Bioactivity 4. Cell Cycle Disruption—Cell cycle effects are of great importance to the characterization of any novel therapeutic agent. This most fundamental cellular process is integral in determining the effects of any drug upon the target cells. After treatment with the tested BQs at previously described conditions, cells were harvested, and stained with 10 µg/ml DAPI (a DNA marker) according to manufacturer's specifications and analyzed with the instrument using image analysis to measure the DAPI intensity as an indicator of the DNA density.

Results and Discussion

Figure 12:
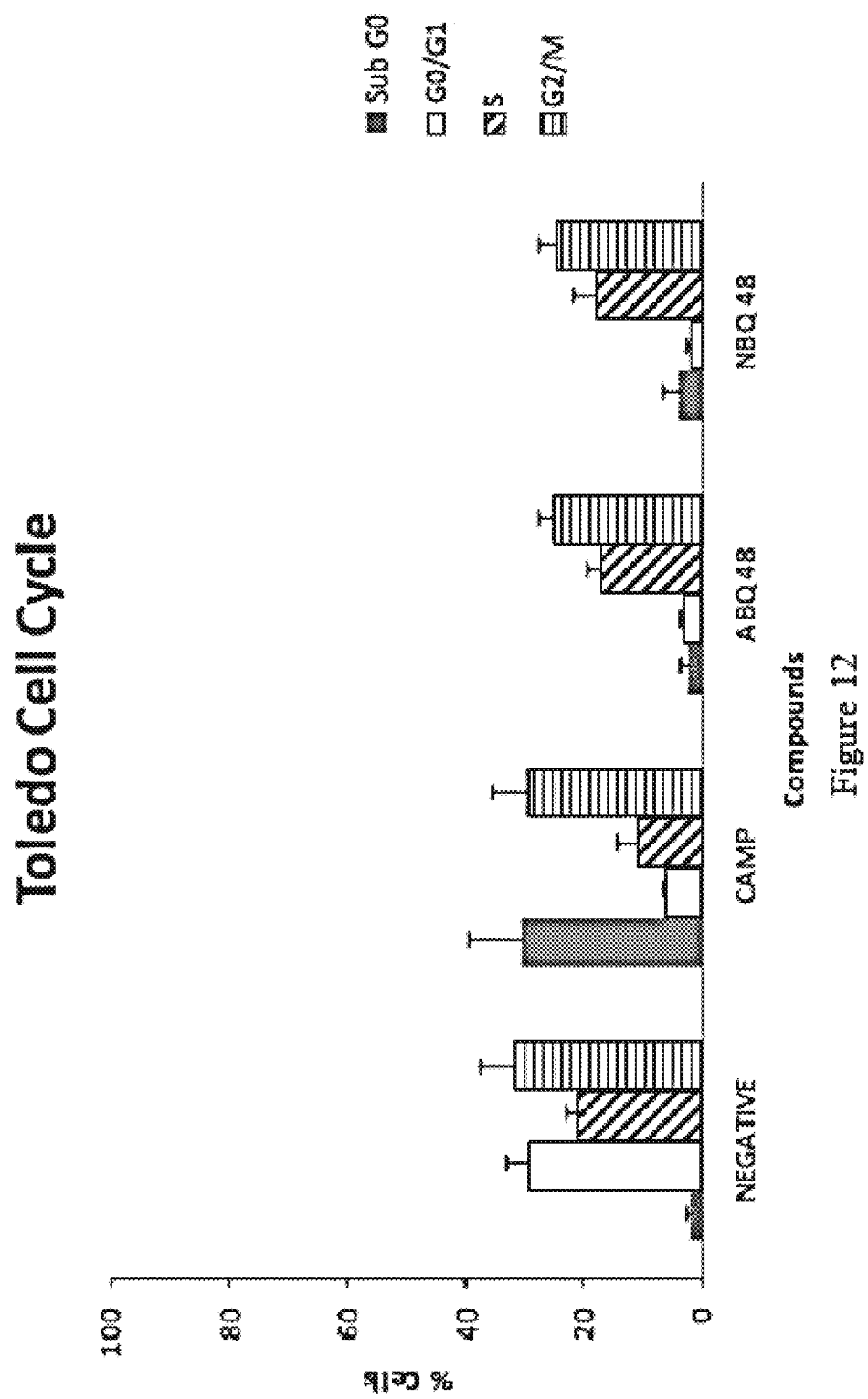
FIG. 12 shows cell cycle disruption analysis of Toledo cells treated with ABQ48 and NBQ48 for 48 hours.

As presented in FIG. 12 the tested ABQ48 induces changes in the cell cycle of the treated cells in comparison with the negative control (none treated cells). Most cells treated with ABQ 48 are arrested at the S/G2 stage in contrast with the control population where cells are distributed among the cells cycle stages.

The biological activities such as generation of DNA fragmentation and cell cycle disruption observed in cells treated with ABQ48 as discussed in Bioactivity 3 and Bioactivity 4 have been observed at different degrees with ABQ 95, ABQ 38, NBQ 95 and NBQ38 on the A431 and TK6 cell lines. The applied method is as reported above:

DNA Fragmentation—Analysis was performed applying the Nucleo counter NC3000 DNA fragmentation assay. Determination of the degree of DNA fragmentation is based on the retention of DAPI, a nucleic acid staining reagent. Prior to treatment with the tested compounds A431 and TK-6 cells were kept in culture at the specified conditions. Cells where then treated with the tested compounds at the respective $IC_{50}$ concentrations (between 25 and 300 µM) DNA fragmentation protocol was as recommended by Nucleo counter NC3000 manufacturer.

Results and Discussion

The tested compounds presented little DNA fragmentation in the tested cell lines.

Over all in tumor cells, such as A431, BQs 95 induced fragmentation at levels close or similar to the negative control in contrast to BQs 38. In TK6 low DNA fragmentation was observed as well.

Cell Cycle Disruption—Cell cycle effects are of great importance to the characterization of any novel therapeutic agent. After treatment with the tested BQS 95 and BQS 38 at previously described conditions, cells were harvested, and stained with 10 µg/ml DAPI (a DNA marker) according to manufacturer's specifications and analyzed with the instrument using image analysis to measure the DAPI intensity as an indicator of the DNA density.

Results and Discussion

Changes in the cell cycle of A431 and TK6 where observed at a higher level with the NBQ 38 than with NBQ 95 with little to none cell cycle effects of the treated cells in comparison with the negative control (none treated cells). Most cells treated with ABQ 48 are arrested at the S/G2 stage in contrast with the control population where cells are distributed among the cells cycle stages.

Reactive Oxygen Species (ROS)—An increase in the generation of Reactive Oxygen Species (ROS) can indicate an apoptotic event involving damage to mitochondria. For determination ROS generation the fluorescent dye 2,7-dichlorofluorescein diacetate (DCFH-DA) was applied a standard protocol based on Park and Park 2007. In this experiment A431 and TK6 cells where treated with ABQ38, ABQ95, NBQ 38 and NBQ 95 at their respective $IC_{50}$.

Results and Discussion

A clear and strong induction of the generation of ROS was observed in A431 treated with ABQ38, ABQ95, NBQ 38 and NBQ 95. In TK6 however, the generation of ROS was close to the level observed in the negative control.

Marker of Bacterial Growth and Antibacterial—The biological activities of the BQs, for example ABQ 48 is further used as a marker of bacterial growth and antibacterial. The fluorescent properties of ABQ 48 an unnatural amino substituted alkaloid with fluorescent properties where applied upon bacterial cells. Two bacterial cell lines *Escherichia coli* (Gram negative) and *Staphylococcus aureus* (Gram positive) were maintained at logarithmic growth in nutrient broth media at 37° C. (NB) and were exposed to 150 µM dose of ABQ 48 for periods of 2, 4 and 6 hours. Cells were washed twice with PBS (Sigma, St. Louis, Mo.) at 2500 rpm and resuspended in 500 µL. Fluorescence in standard units (FSU) was measured using a Modulus fluorometer (Promega, Sunnyvale, Calif.). Three measurements were obtained from each sample. Values were then averaged and background corrected using the negative control values. Results indicate that Gram negative cells fluoresce faster than gram negative. After a 2 hour exposure Gram negative stained as observed by an increase in the fluorescence in standard units (FSU) in contrast to Gram positive cells which fluoresce after a 4 hour exposure.

Use of ABQs as antibacterial is based on a standard Kirby-Bauer antimicrobial susceptibility test where the growth inhibition of a known bacterial colony in the presence of the ABQS is measured.

BQs Drug-Likeness Analysis—FIGS. 13 and 14 include the drug-likeness and Mol Log P of ABQ-2, 38, 48, 91 and 95 and other compounds. ABQ-95 displays the highest drug-likeness (0.43) among those already reported in Ser. No. 12/416,174. Log P is the Log of the partition of the compound between an organic phase (e.g. octanol) and an aqueous phase (e.g. buffer) at a pH. BQs are lipophilic cations, and a correlation has been suggested between Log P and the preference of this type of compounds to interact with the mitochondria. Therefore, it is of interest to correlate mitochondrial permeabilization, one of the bioactivities we have determined for ABQs, and Mol Log P. Results shown in FIG. 13 and FIG. 14 serves as a guide to design and synthesize compounds with increased drug-likeness and their Mol Log P.

Figure 15:
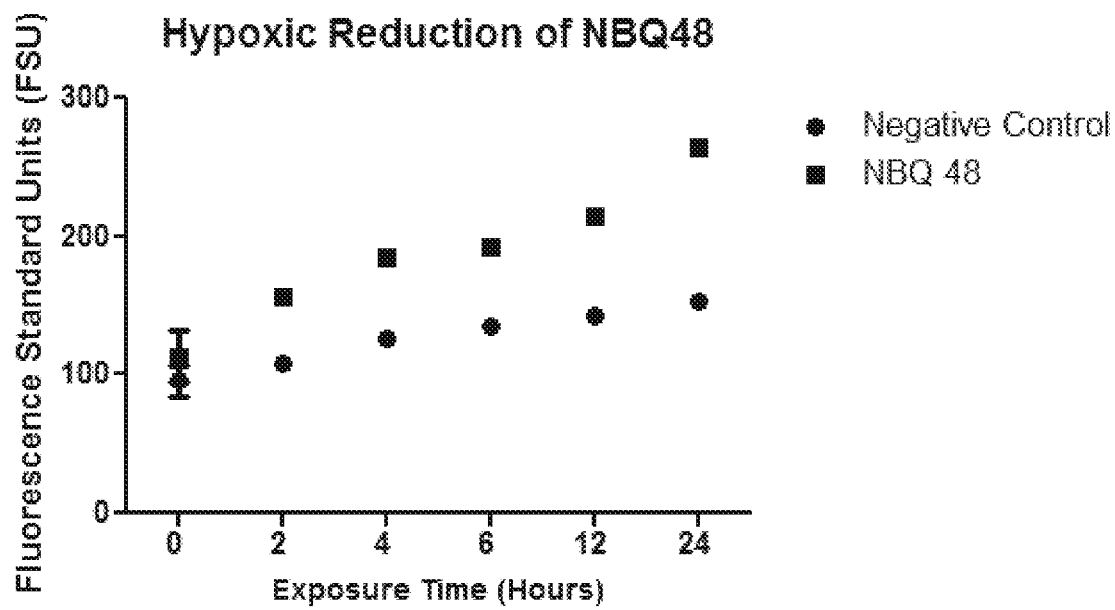
FIG. 15 through FIG. 16 represents Fluorescence uptake of NBQ48 on hypoxic reduction as a function of time (0 to 24 hours).

FIG. 15 is directed to the fluorescent detection of metabolically actives cells under Hypoxic Environment. The reagent NBQ48 is applicable to determine the metabolic activity of cells or tissues under low or no oxygen content (hypoxic environment). The reagent NBQ48 is a non-fluorescent compound that can be transformed into a fluorescent metabolite by hypoxic cells that are alive and metabolically active.

Figure 16:
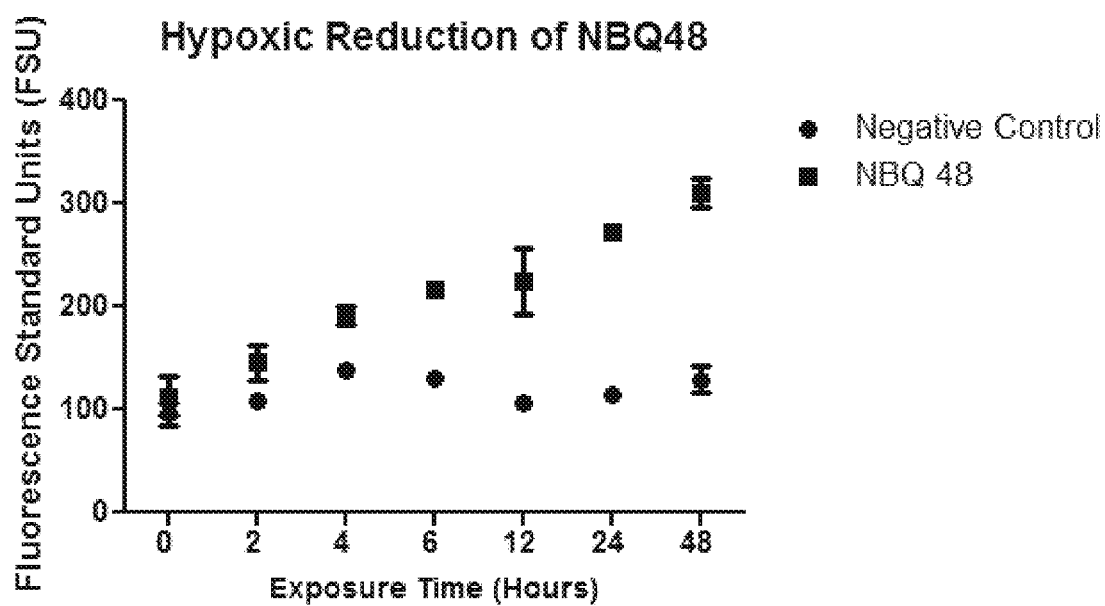
Figure 17:
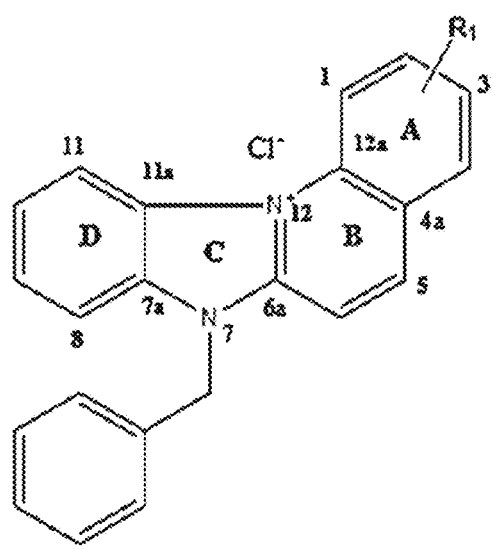
FIG. 17 shows the general Structure of ABQ and NBQ.
Figure 18:
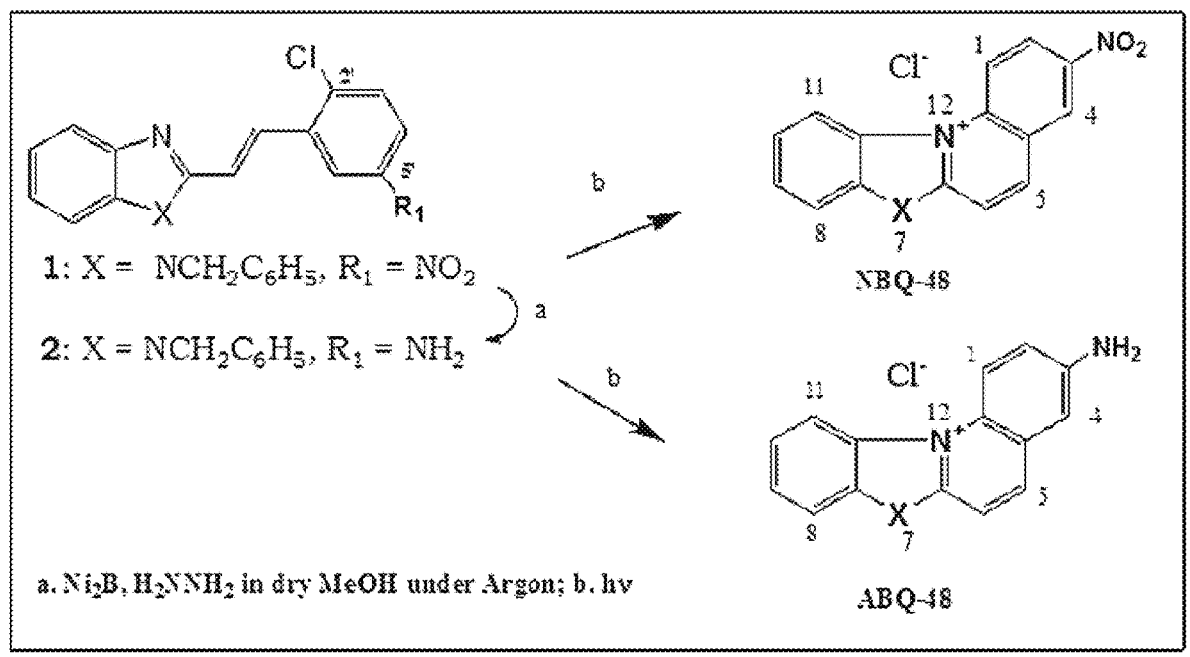
FIG. 18 shows the Synthesis of ABQ48 and its nitro substituted analog NBQ48.

FIG. 15 graphically illustrates tumor cells, such as Toledo cells, under hypoxic conditions treated at various time points. At time cero (panel A) fluoresce emission is not observed since NBQ 48 is not fluorescent. After 2, 12 and 24 hours (panel B, C & D) of exposure metabolically active cells transform the NBQ48 into a florescent metabolite. Control cells under aerobic conditions do not fluoresce at similar exposure treatments. FIG. 16 illustrates the fluorescent based reduction of A431 cells incubated as describe in FIG. 15.

Compound Synthesis of NBQ-48 and ABQ-48

The synthesis of 3-nitro- and 3-amino-7-benzylbenzimidazo[3,2-a]quinolinium chlorides (NBQ-48 (NSC D-763393) and ABQ-48 (NSC D-763307), respectively, is depicted in Scheme 1. These compounds were prepared by a modification previously described methodology in documents Synthesis and biological activity of benzothiazolo- and benzoxazolo[3,2-a]quinolinium salts, Journal of medicinal chemistry, 1982, 25(11), 1378-1381 and Comparison of the Nucleic Acid Covalent Binding Capacity of Two Nitro-Substituted Benzazolo[3,2-a]quinolinium Salts upon Enzymatic Reduction, *Toxicology in Vitro*, 2007, 21 (6), 1155-1164 (both document included by reference). The sequence commences with the condensation of 1-benzyl-2-methyl-benzimidazole with 2-chloro-5-nitrobenzaldehyde in boiling acetic anhydride to yield (E)-1-benzyl-2-(2'-chloro-5'-nitrostyryl)benzimidazole (1). Photolysis of 1 as described in [13] produced NBQ-48 in good yield. The (E)-1-benzyl-2-(2'-chloro-5'-aminostyryl)benzimidazole (2) was obtained by the catalytic reduction of 1, using hydrazine and nickel boride in methanol solution under an argon atmosphere. Photochemically induced cyclization of 2 gave ABQ-48 in excellent yield. All compounds were characterized by 1D and 2D $^1$H NMR spectroscopy, and high resolution mass spectrometry (HRMS). The assignments of NMR proton and 13 carbon chemical shifts of these compounds are included as Supplementary Information.

Methodology

The National Cancer Institute (NCI) 60 human tumor cell line screen uses genetically characterized cells to determine biological activity against various cell lines [14]. The panel is comprised of various cell types representing some of the most important cancer types[15]. Two of the benzazolo[3,2-a]quinolinium salts i.e. NBQ 48 (NSC: D-763303) and ABQ 48 (NSC: D-763307) were tested at a dose of 10 µM on the entire cell line panel. The complete details of the NCI-60 cell line screening are describe in document Feasibility of drug screening with panels of human tumor cell lines using a microculture tetrazolium assay. *Cancer research,* 1988, 48(3), 589-601 (here included by reference).

Briefly, the cancer cells are grown in RPM1 1640 medium for 24 hours. Experimental compounds dissolved in DMSO are incubated with cells at 10 µM. After incubation the cells are stained with sulforhodamine B and the absorbance is read on a plate reader. The data reported as a mean graph are shown in the drawings FIG. 21 through FIGS. 24A-24I. For five dose study the test compound is incubated with cells at five different concentrations with 10-fold dilutions, from $10^{-4}$ M, $10^{-5}$, $10^{-6}$, $10^{-7}$, and $10^{-8}$ M. Rest of the procedure is similar to the one dose experiment. After measurement, the ($GI_{50}$) is calculated from time zero, control growth, and the five concentration absorbance. Inhibitory concentrations ($LC_{50}$) represent the average of two experiments.

Results

Experimental Procedures

All experiments were carried out in dry glassware (2 h, 125° C.) under an open atmosphere. Irradiations were conducted at room temperature using a Rayonet Photochemical Reactor fitted with 350 nm lamps. The melting point determined in a capillary tube using a Stuart Melt-Temp apparatus (Burlington, N.J.). The $^1$H and $^{13}$C NMR spectra were recorded using a General Electric (Fairfield, Conn.) QE-300 (5 mm C/H dual probe) operating at frequency of 300.15 and 75.48 MHz for $^1$H and $^{13}$C, respectively equipped with Nicolet 1280 data system and 293-C programmer or a Bruker (Billerica, Mass.) AVANCE AV-500 using a 5 mm broadband probe; $^1$H 500.13 MHz; $^{13}$C 125.75 MHz The proton data were referenced to tetramethylsilane at δ 0.0 ppm, chloroform at δ 7.26 ppm or methyl sulfoxide at δ 2.49 ppm. The nuclei of $^{13}$C were referenced to the center peak of 1:1:1 multiplet of deuteriochloroform at δ 77.0 ppm or the multiplet of DMSO-d6 was assigned at δ 39.5 ppm.

Synthetic Procedures

The photochemical cyclization and work-up procedure for a synthesis of benzazolo[3,2-a]quinolinium salts was described in document "Synthesis and biological activity of benzothiazolo- and benzoxazolo[3,2-a]quinolinium salts. Journal of medicinal chemistry, 1982, 25(11), 1378-1381", here included by reference. However in the current disclosure a green procedure for the synthesis of benzazolo[3,2-a]quinolinium salts similar to that described, except, that the corresponding (E)-2-(2-chlorostyryl)benzazole was dissolved in 150-250 mL of a 2:2:1 (heptane:dioxane:bromobenzene) solution [13,18]. Benzene as a solvent in this reaction constitutes a green chemistry procedure.

(E)-1-Benzyl-2-(2'-chloro-5'-nitrostyryl)benzimidazole (1). Following the general procedure, 1-benzyl-2-methyl-benzimidazole (14.7 g, 66.0 mmol) condensed with 2-chloro-5-nitrobenzaldehyde (12.2 g, 66.0 mmol) in boiling acetic anhydride to yield 24.1 g (94%) of product. Recrystallization from chloroform gave 22.1 g (86%) of 1: mp 201-202 C.°: $^1$H NMR (DMSO-$d_6$, 300 MHz) δ 8.95 (d, J=2.4 Hz, 1 H, aromatic), 8.18 (dd, J=9.0, 2.4 Hz, 1 H, aromatic), AB pattern at 8.22 and 8.00 (J=15.6 Hz, trans CH=CH, 2H), 7.84 (d, J=9.7 Hz, 1 H, aromatic), 7.72-7.70 (m, 1 H, aromatic), 7.55-7.51 (m, 1 H, aromatic), 7.35-7.17 (m, 7 H, aromatic), 5.80 (d, J=27.6 Hz, 2 H, CH$_2$Ph); $^{13}$C NMR (DMSO-$d_6$, 300 MHz) δ 45.9, 110.8, 119.1, 119.9, 122.0, 122.6, 122.8, 124.2, 126.7, 127.5, 128.7, 129.1, 131.3, 134.9, 135.5, 137.3, 139.1, 142.9, 147.0, 149.8. Anal. calcd for C$_{22}$H$_{16}$ClN$_3$O$_2$: C, 67.78; H, 4.14; N, 10.78. Found: C, 67.85; H, 4.16; N, 10.76.

(E)-1-Benzyl-2-(2'-chloro-5'-aminostyryl)benzimidazole (2). This compound was obtained from the reduction of (E)-1-benzyl-2-(2'-chloro-5'-nitrostyryl)benzimidazole-zole (1) with nickel-boride hydrazine in refluxing anhydrous methanol as described [11] to yield 2 as a yellow solid: mp 150-152 C.°; $^1$H NMR (DMSO-d6, 400 MHz) δ 8.13 and 7.39 (AB pattern, J=15.6 Hz, trans CH=CH, 2H), 7.69 (dd J=6.80 and 1.6 Hz, 1H), 7.54 (d, J=6.80, 1H, 7.3 to 7.2 (complex pattern, 9H), 6.65 (d J=8.48, 1H), 5.72 (s, 2H, Ph CH$_2$), 5.27 (s, 2H, NH$_2$); HRMS (ESI): m/z Calcd. for C$_{22}$H$_{19}$ClN$_3$ (MH+) 360.12576. Found: 360.12620 (−1.23 ppm).

7-benzyl-3-nitrobenzimidazolo[3,2-a]quinolinium chloride (NBQ-48: NSC: D-763303). (E)-1-benzyl-2-(2-chloro-3-nitrostyryl)benzimidazole (0.50 g, 1.3 mmol) was dissolved in 150 mL of a 2:2:1 (heptane:dioxane: bromobenzene) mixture and photolyzed as described [13] to give the 350 mg (70%) of the title compound as an off white solid: mp 230 C.° (dec.) $^1$H NMR (DMSO-$d_6$, 300 MHz) 9.45 (d, J=9.6 Hz, 1 H, aromatic), 9.40 (d, J=2.7 Hz, 1 H, aromatic), 9.20 (d, J=9.3 Hz, 1 H aromatic), 9.07 (d, J=9.6 Hz, 1 H, aromatic), 8.78 (dd, J=9.0, 2.7 Hz, 1 H aromatic), 8.76 (d, J=9.3 Hz, 1 H, aromatic), 3.25 (d, J=9.3 Hz, 1 H, aromatic), 7.95-7.92 (m, 2 H, aromatic), 7.48-7.33 (m, 5 H, aromatic); $^{13}$C NMR (DMSO-$d_6$, 300 MHz) δ 48.7, 111.5, 114.3, 117.7, 119.9, 125.0, 127.0, 127.7, 127.9, 128.0, 129.0, 129.6, 129.8, 132.7, 134.0, 137.3, 141.0, 144.5, 145.8; IR (KBr) 3080.0, 2920.0, 1653.4, 1616.8, 1569.5, 1524.3, 1473.1, 1456.3, 1427.7, 1398.4, 1384.9, 1346.2, 1158.3, 1095.5, 812.9, 737.0, 706.0, 624.0, 401.2 cm$^{-1}$. Compound was analyzed as the perchlorate derivative: UV (95% EtOH) λmax/nm (ε M$^{-1}$cm$^{-1}$): 361 nm (ε 40000), 348 (50000), 332 (50000), 287 (90000), 274 (80000), 263 (80000), 216 (90000). Anal. calcd for C$_{22}$H$_{16}$ClN$_3$O$_6$: C, 58.22; H, 3.55; N, 9.26. Found: C, 58.54; H, 3.29; N, 9.52.

7-Benzyl-3-aminobenzimidazo[3,2-a]quinolinium chloride (ABQ-48: NSC D-763307). (E)-7-benzyl-2-(2'-chloro-5'-aminostyryl)benzimidazole (50.0 g, 1.39 mmol) was dissolved in 150 mL of a 2:2:1 heptane:dioxane:bromobenzene mixture and photolyzed as described [13] to give the 250 mg (50%) of title compound as a bright yellow solid: mp 270 C.° (dec.); UV-vis (PBS 7.4 Buffer) λmax/nm (ε M$^{-1}$cm$^{-1}$): 259 (2.94×10$^4$), 330 (1.29×10$^4$), 342 (1.18×10$^4$), 371 (4.54× 10$^3$). $^1$H NMR (500 MHz, DMSO-d6) δ 9.06 (d, J=8.6 Hz, 1H), 8.90 (d, J=9.3 Hz, 1H), 8.57 (d, J=9.6 Hz, 1H), 8.28 (d, J=9.6 Hz, 1H), 8.13 (dd, J=8.4, 1.2 Hz, 1H), 7.84 (ddd, J=8.2, 7.3, 1.0 Hz, 1H), 7.78 (ddd, J=8.5, 7.3, 1.3 Hz, 1H), 7.43 (dd, J=9.2, 2.7 Hz, 1H), 7.40-7.28 (m, 5H), 7.25 (d, J=2.7 Hz, 1H), 6.08 (s, 2H), 6.02 (s, 2H). $^{13}$C NMR (126 MHz, DMSO-d6) δ 148.04, 141.41, 139.56, 134.52, 131.96, 128.78, 128.12, 127.87, 127.78, 127.02, 125.88, 125.60, 124.72, 121.48, 118.07, 116.82, 112.97, 109.98, 108.23, 46.88. HRMS (ESI): m/z Calcd. for C$_{22}$H$_{18}$N$_3$ (without the chloride counter ion) 324.14952. Found: 324.14812 (Δ −4.33 ppm).

NCI-60 Human Tumor Cell Line Screen

All the one-dose data of these compounds is reported as a mean of the growth percent of BQ exposed cells. One dose assay results are relative to control and number of cells at time 0. Growth inhibition values are placed from 0 to 100 whereas lethality is reflected in values less than 0. A sample obtained value of 100 means that no growth was inhibited. If the value is for example 30 then growth inhibition is 70%. If a sample has a value of −30 then this means 30% lethality, conversely if the value would be −100 the all cells in the sample are dead. The supporting information in FIG. 19 presents a summary of these results.

Figure 20:
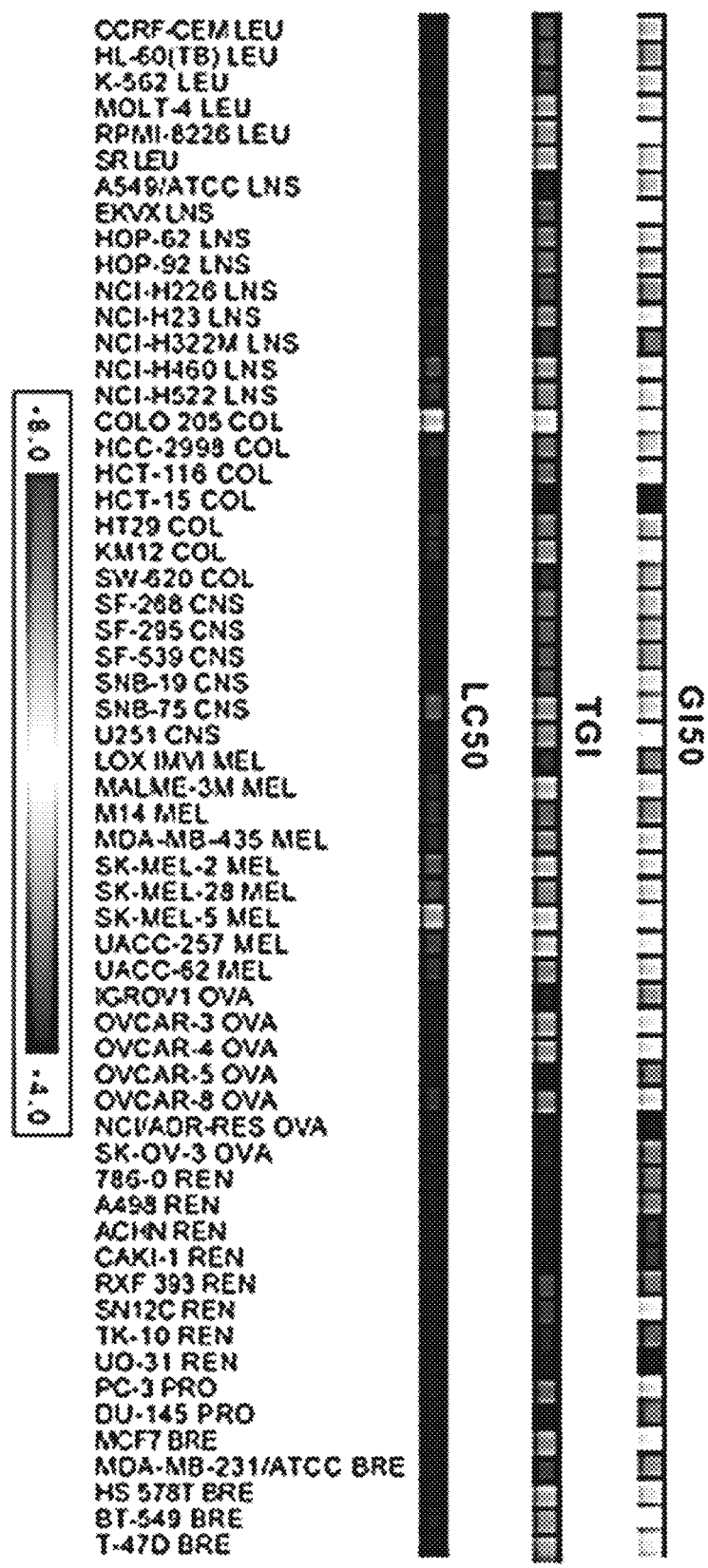
FIG. 20 shows five dose Response Graphs (individual panel) for ABQ-48 (NSC 763307) showing the percentage growth inhibition ($GI_{50}$), total growth inhibition (TGI) and the inhibitory concentrations ($LC_{50}$) in the NCI 60 human cancer cell line screen.
Figure 23:
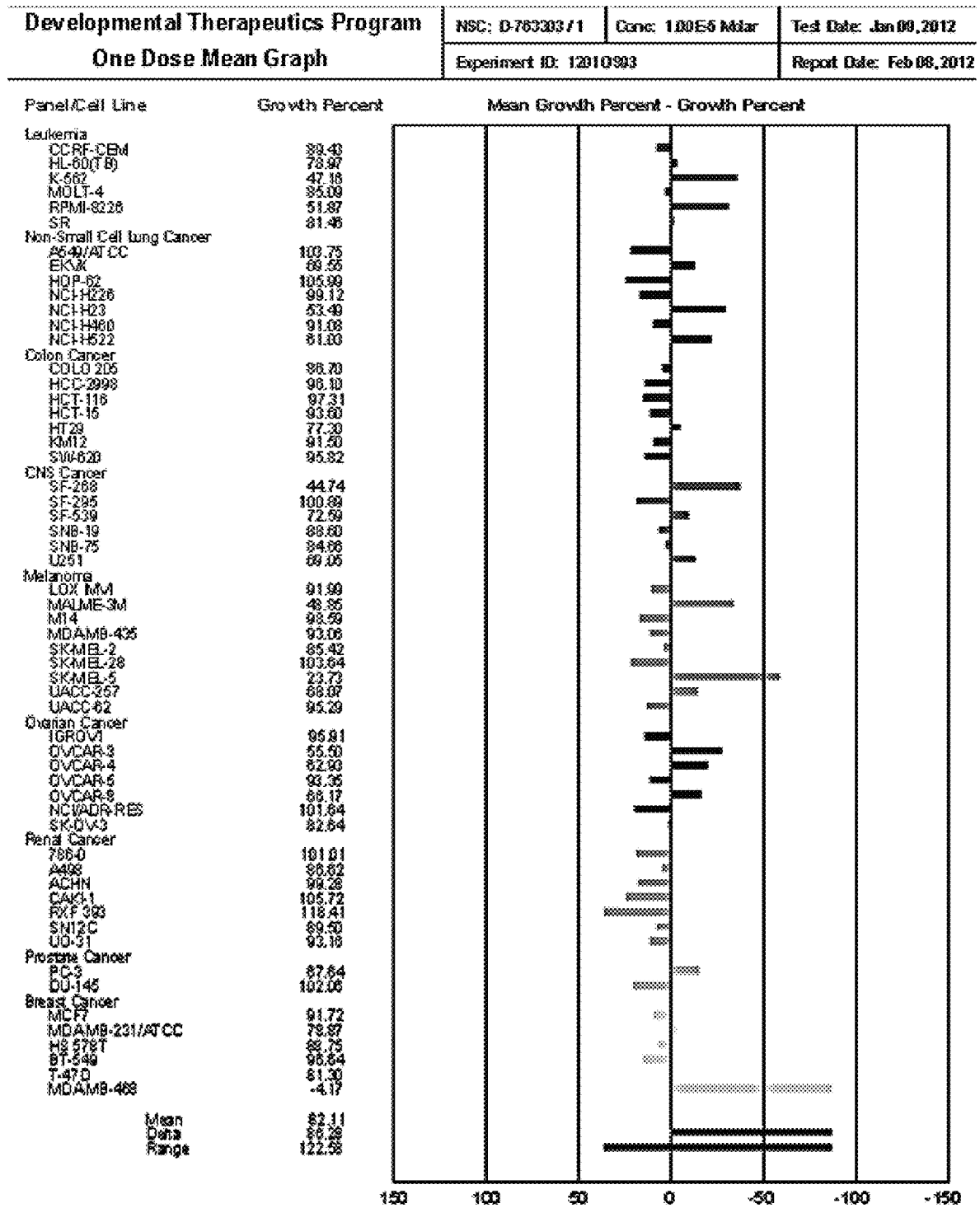
FIG. 23 shows one dose mean data graph for NBQ-48 (NSC 763303) in the NCI 60 human cancer cell line screen.
Figure 24A:
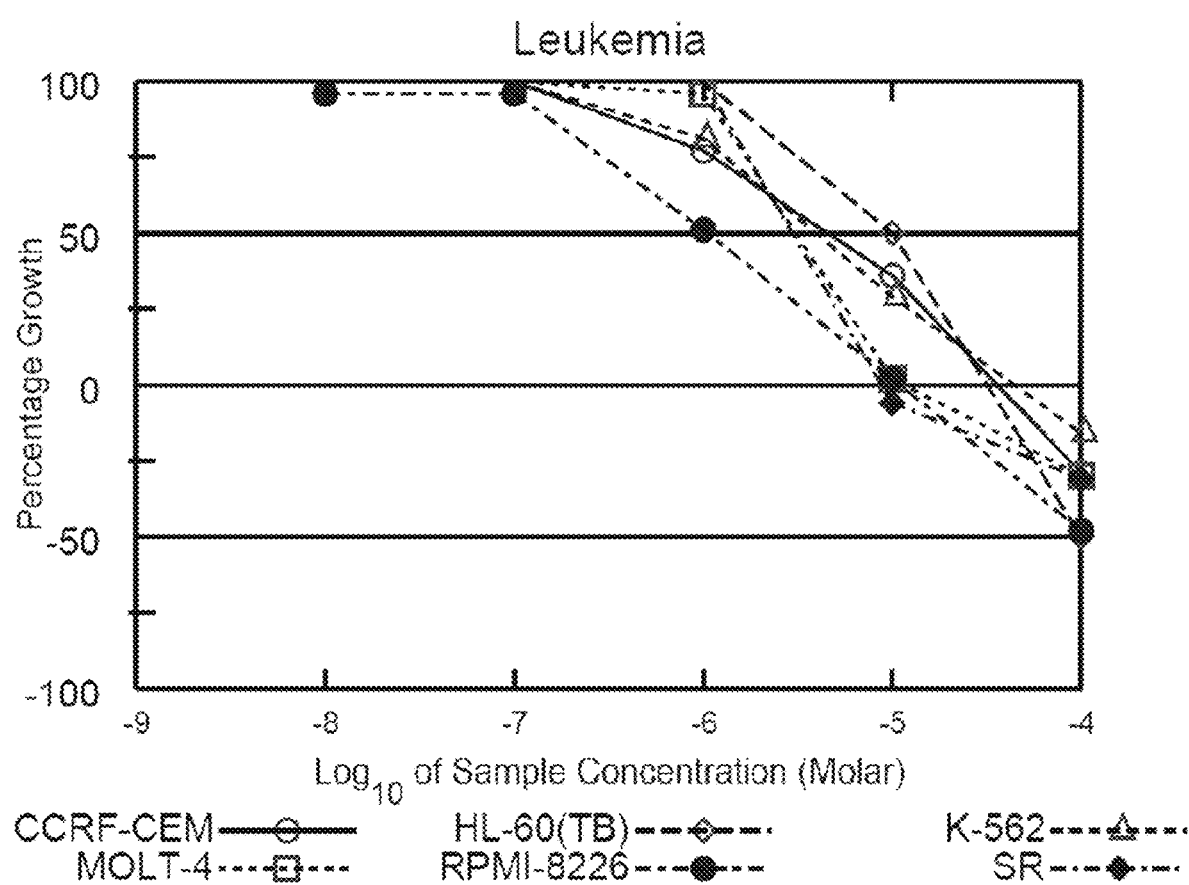
FIGS. 24A-24I show five dose Drug Response curves for compound ABQ-48 (NSC 763307) graphed as percentage of growth vs. $log_{10}$ sample concentration.
Figure 24B:
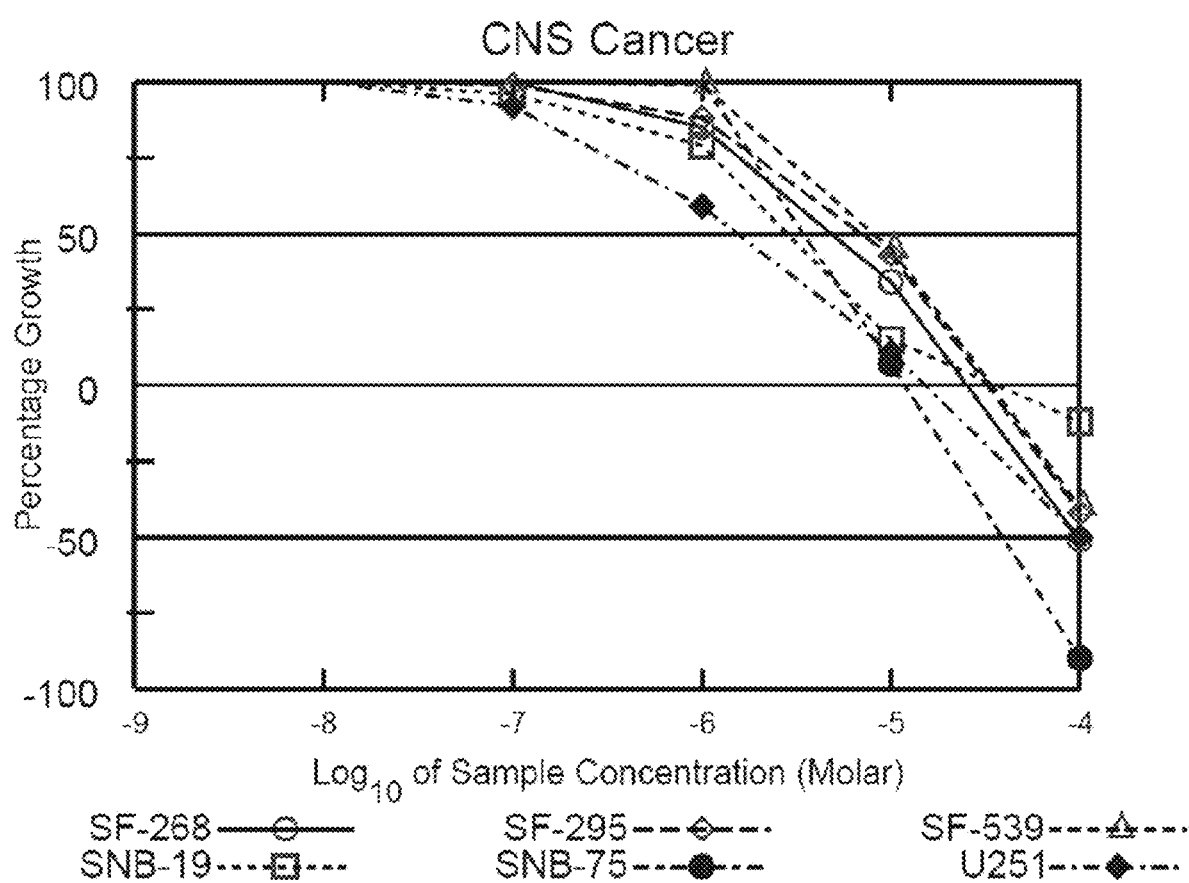
Figure 24C:
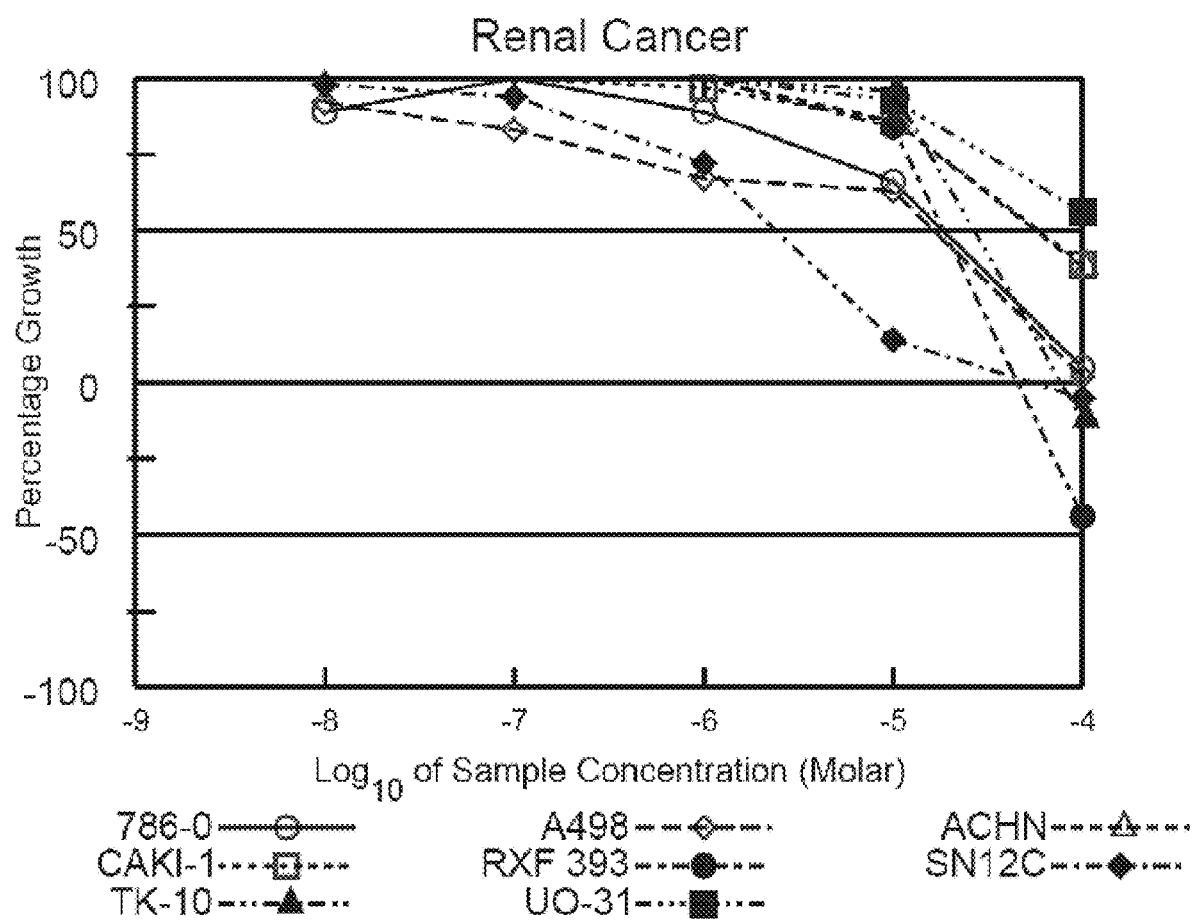
Figure 24D:
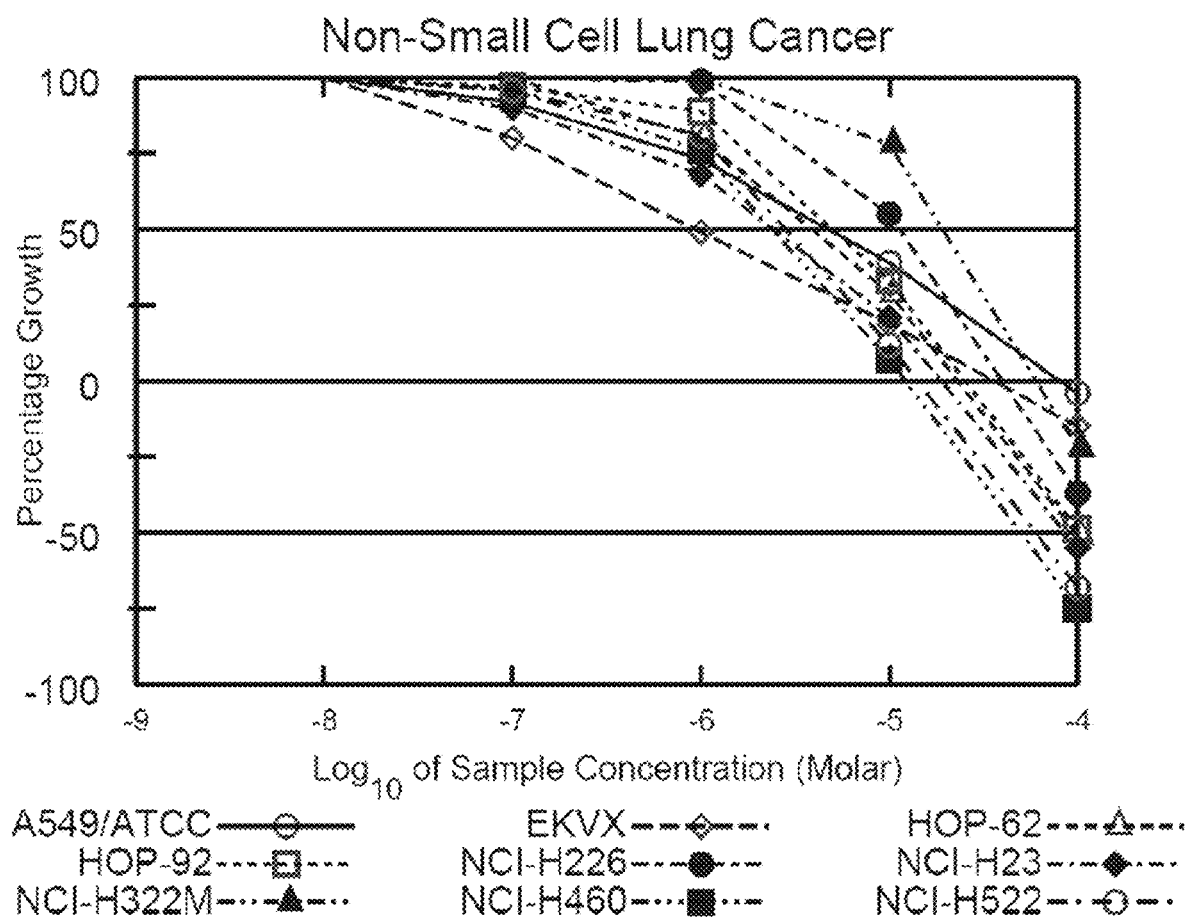
Figure 24E:
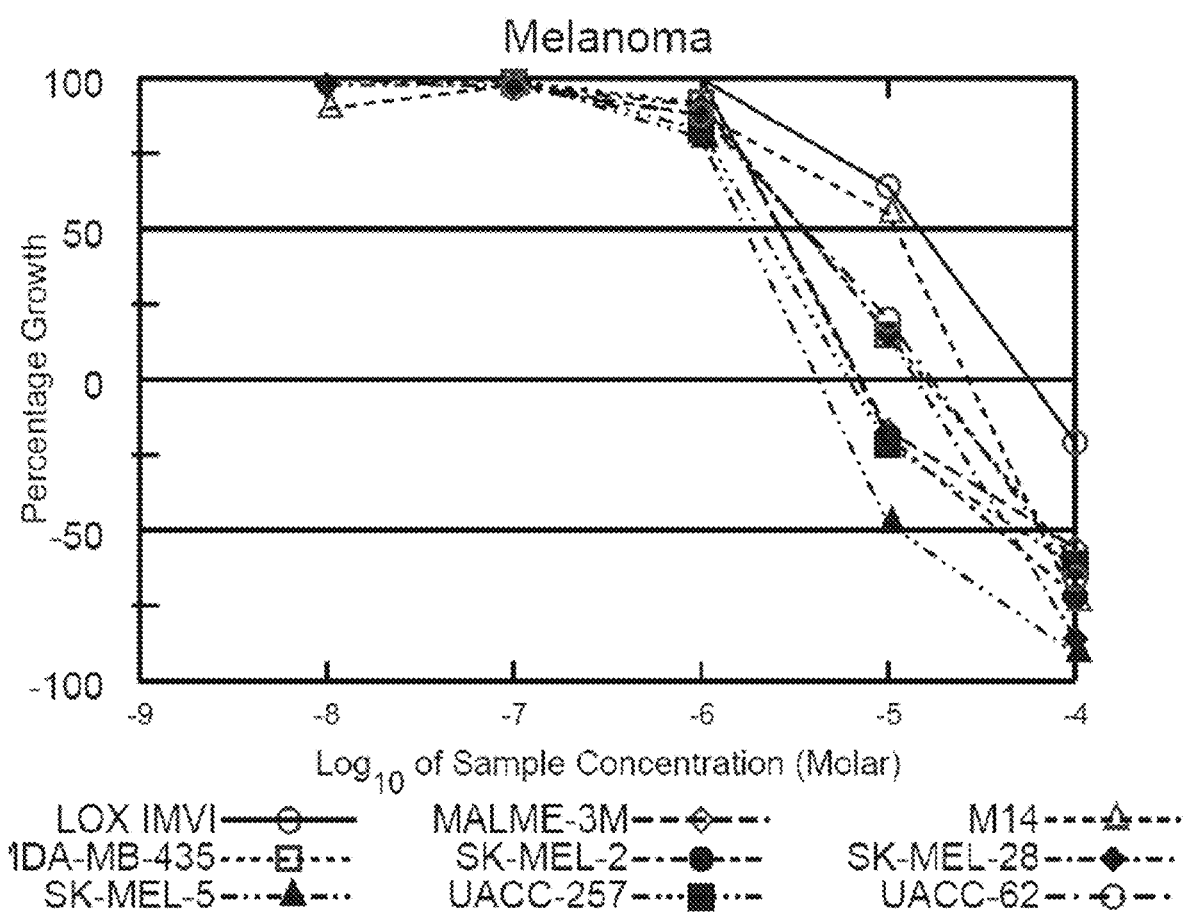
Figure 24F:
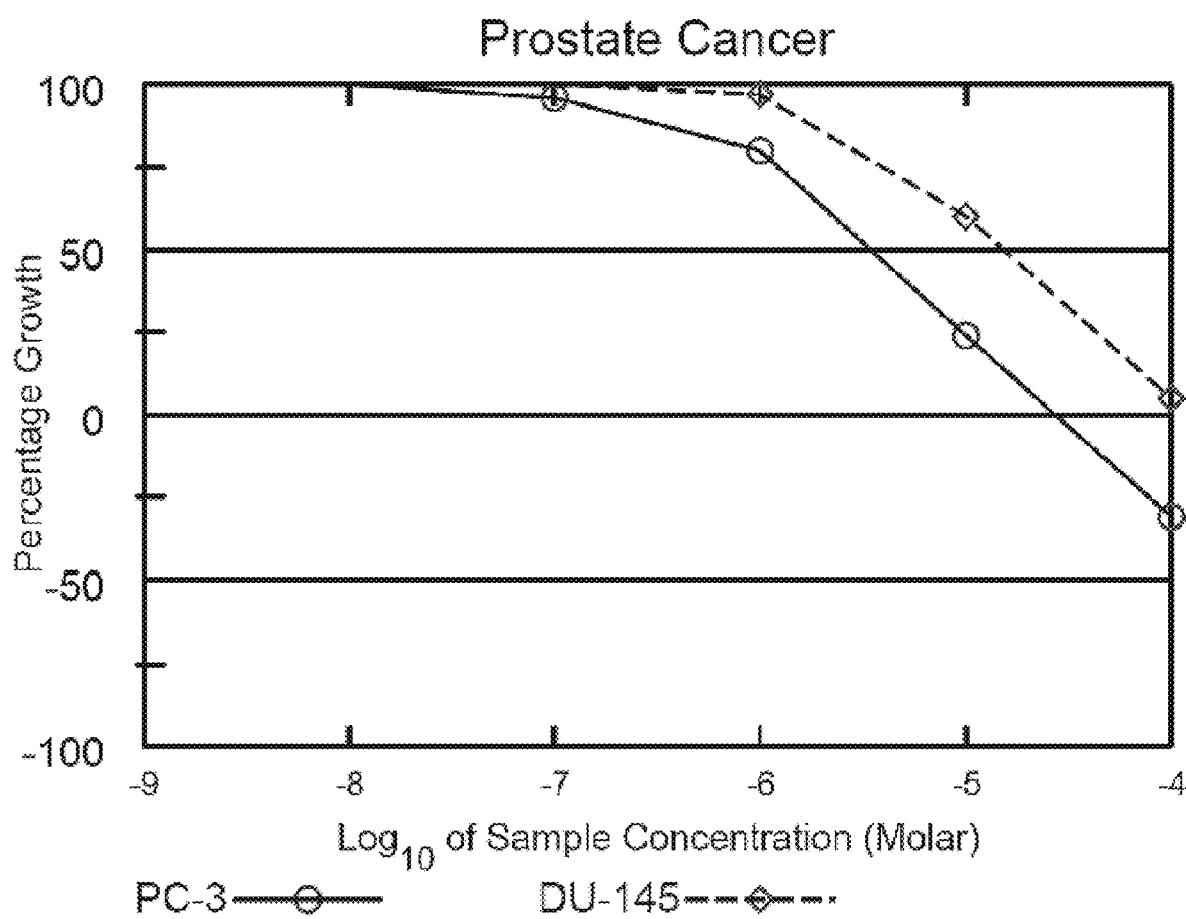
Figure 24G:
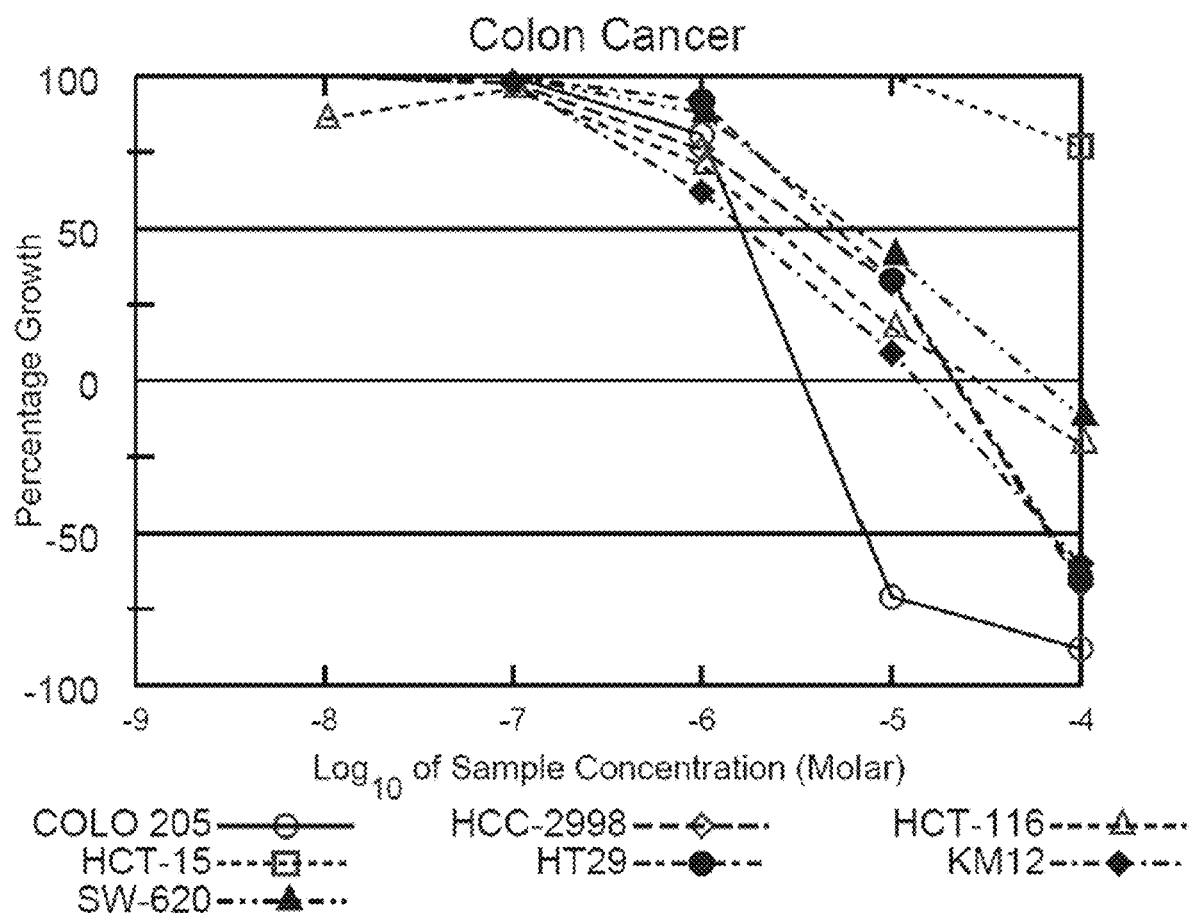
Figure 24H:
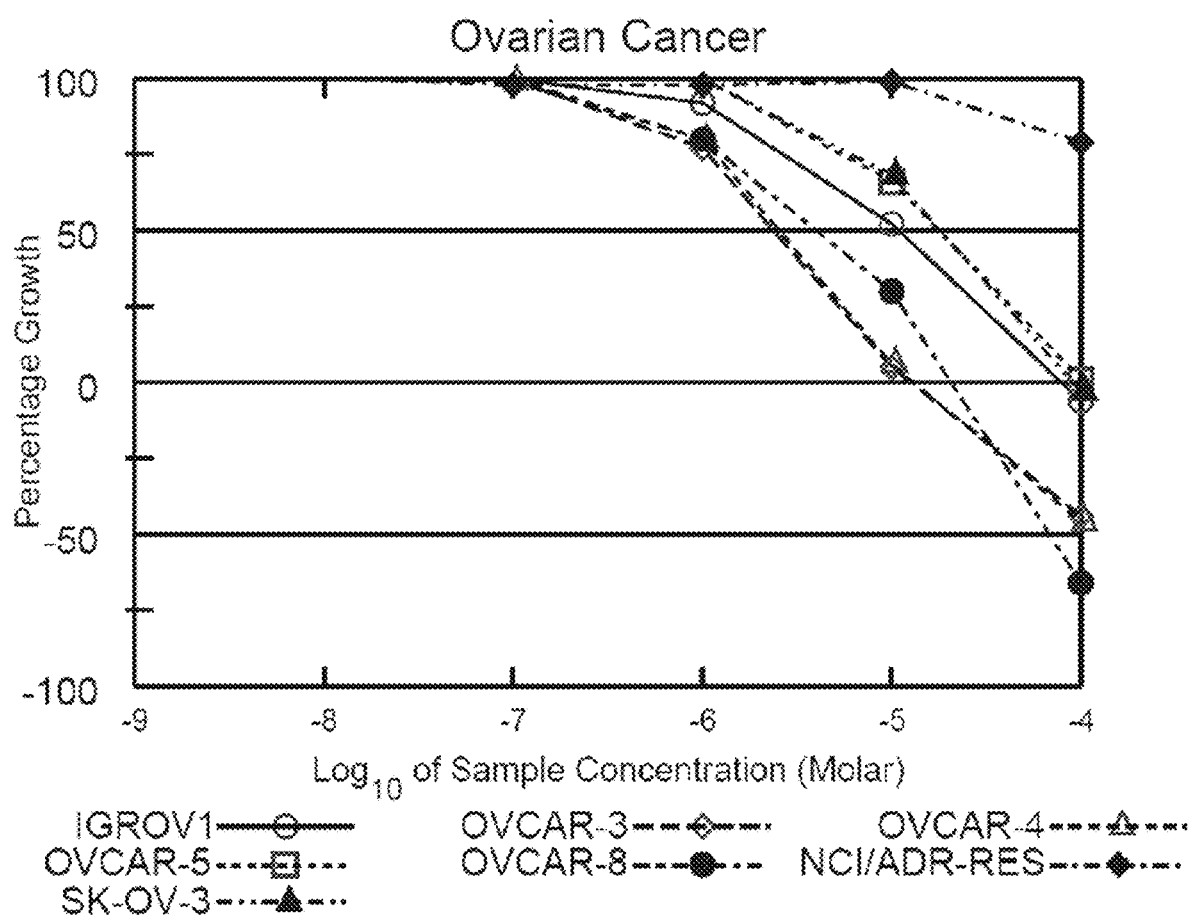
Figure 24I:
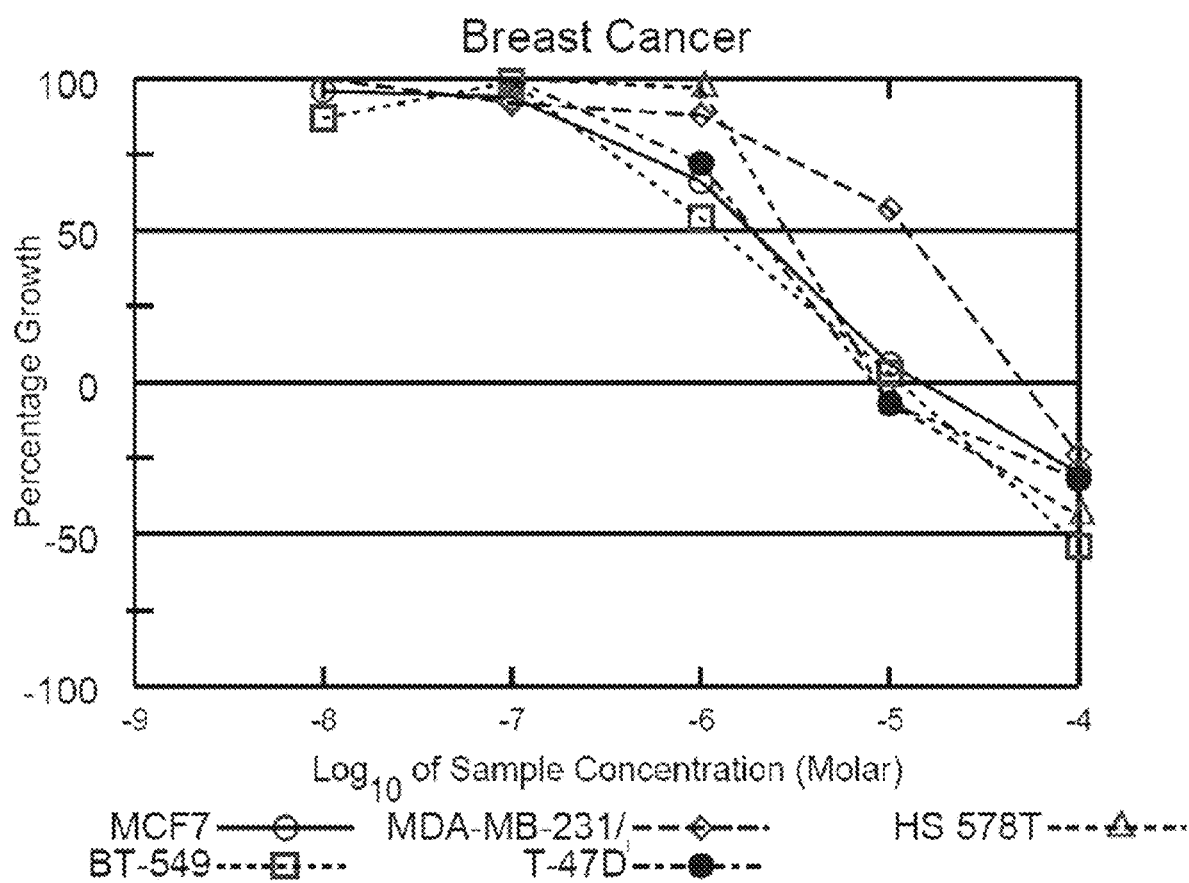

The data presented show that ABQ 48 with an amino group, at position 3 in ring A is highly effective in inhibiting the growth inhibition in several cancer cell lines. However, its analog NBQ 48 with nitro group is less effective in inhibiting most of the cell lines. The change from a nitro to an amino substituent, not only causes a change in the electronic demand of these compounds, but also their ability to form hydrogen bonds and other relevant physical properties that may be responsible for their ability to interact with cellular components. Several results indicate that the targets of these compounds are probably DNA and topoisomerase II. ABQ 48 shows >90% growth inhibition in KM12, U251 & SK-MEL-5; and >70% growth inhibition in several cell lines. As per the NCI's screening criteria ABQ 48 showed greater than 60% growth inhibition in no less than 8 cell lines, and was therefore, selected for a five dose response study. The results of this screen i.e. percentage growth inhibition ($G_{50}$), total growth inhibition (TGI) and the inhibitory concentrations ($LC_{50}$) are shown as the heat map in FIG. 20. The growth inhibition graphs for nine different panels and detailed results for this screen on all 60 human cancer cell lines are given as supplementary information.

The synthesis of NBQ-48 and ABQ-48 was achieved by a modified procedure in which the 2-chloro-5-nitro- or 2-chloro-5-aminostyrylbenzimidazole was photocyclized using a 2:2:1 heptane:dioxane:bromobenzene mixture. The complete proton and carbon-13 chemical shifts assignments of ABQ-48: NSC D-763307 and NBQ-48: NSC D-763303, respectively, is shown in FIG. 21 and FIG. 22. The most downfield proton resonances in NBQ-48 are at δ (ppm) 9.44 (H1), 9.40 (H4), 9.19 (H11), whereas in ABQ-48 the most downfield proton resonances appear at δ (ppm) 9.06 (H11), 8.90 (H1), and 8.57 (H5). In general, all the proton resonances are displaced downfield in NBQ-48 with respect to ABQ-48, consistent with a strong electron withdrawing ability of the nitro group in NBQ-48 and a robust electron resonance donating ability of the amino group in ABQ-48.

The increased biological activity of ABQ-48 compared to that of NBQ-48 can be rationalized using molecular properties prediction, drug-likeness using Molinspiration (Molinspiration Cheminformatics, Slovak Republic). According to these calculations both compounds obey Lipinski's rule of five, however, the presence of an amino group in ABQ-48 incorporates two hydrogen bond donors thus increasing its ability to display stronger interactions with enzymes. Furthermore, these calculations indicate ABQ-48 is a better enzyme inhibitor than NBQ-48. The biological activity of these compounds appears to be closely related to their differences in electronic demand, but also on their ability to form hydrogen bonds and on other relevant physical properties that may be for their ability to interact with cellular components. Several results from our laboratory indicates that the targets of these compounds are probably DNA, topoisomerase II. It has been reported that biological activity in quinoline compounds upon different tissues varies with changes in substituent groups and is dependent on the electron donating properties. Our results present a clear difference in the biological activity of these two BQS, which also includes a cell death mechanism.

Synthesis and Biological Activity of 3,4,5- and 2,3,4- (Trimethoxybenzyl) benzimidazo[3,2-a]quinolinium Chlorides.

The biological activity and outcome of certain compounds can be determined by small structural differences. Some compounds can have substituent groups that may favor affinity for a certain enzyme and improve the desired therapeutic effect. In this disclosure we disclose the biological activities of derivatives of 3-nitro-7-benzyl- and 3-amino-7-benzylbenzimidazo[3,2-a]quinolinium chlorides (NBQ-48 and ABQ-48, respectively), with methoxy substituents at the N-7-benzyl ring. This substitution leads to two different series, namely, 3-nitro-7-(3,4,5-trimethoxybenzyl)- and 3-amino-7-(2,3,4-trimethoxybenzyl)benzimidazo[3,2-a]quinoliniun chlorides derivatives. The resulting compounds when submitted to the NCI 60 human cancer cell line screen presented varied cell toxicity effects. In the case of the 3,4,5-trimethoxybenzy series both the 3-nitro and the 3-amino substituted compounds showed low activity in this screen. In contrast, in the 2,3,4-trimethoxybenzyl series the 3-nitro, and especially the 3-amino results indicate excellent activity in the NCI screen. In view of these results we decided to study further the activity of the 2,3,4-trimethoxybenzyl (2,3,4TOM) series. More specifically we analyzed the apoptosis induction, mitochondrial damage and DNA fragmentation of NBQ 234 TOM and ABQ 234TOM in colon 205 cancer cells at 10 uM and 20 µM. The structure, numbering system and NCI NSC numbers for these new compounds is shown in Scheme 1.

Figure 35:
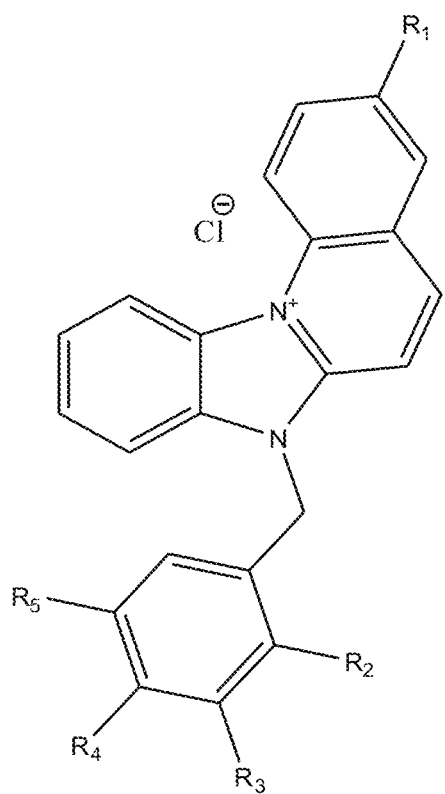
FIG. 35 shows the general structure of the ABQS and NBQS derived from ABQ-48.

Scheme 1. The general structure of the ABQS and NBQS derived from ABQ-48 is presented in FIG. 35 and Table 1.

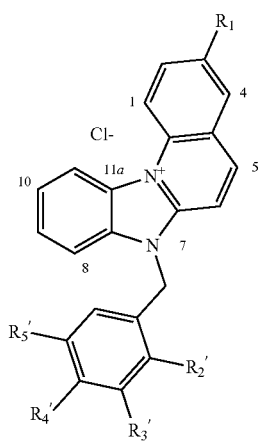

TABLE 1

List of New NBQS and ABQS derived from NBQ-48 and ABQ-48 prepared.

| NSC No. | Compound | $R_1$ | $R_2'$ | $R_3'$ | $R_4'$ | $R_5'$ |
|---------|----------|-------|--------|--------|--------|--------|
| 777569  | 1        | $NO_2$ | H     | $OCH_3$ | $OCH_3$ | $OCH_3$ |
| 783044  | 1a       | $NH_2$ | H     | $OCH_3$ | $OCH_3$ | $OCH_3$ |
| 787913  | 2        | $NO_2$ | $OCH_3$ | $OCH_3$ | $OCH_3$ | H |
| 788870  | 2a       | $NH_2$ | $OCH_3$ | $OCH_3$ | $OCH_3$ | H |

Materials and Methods

Figure 36:
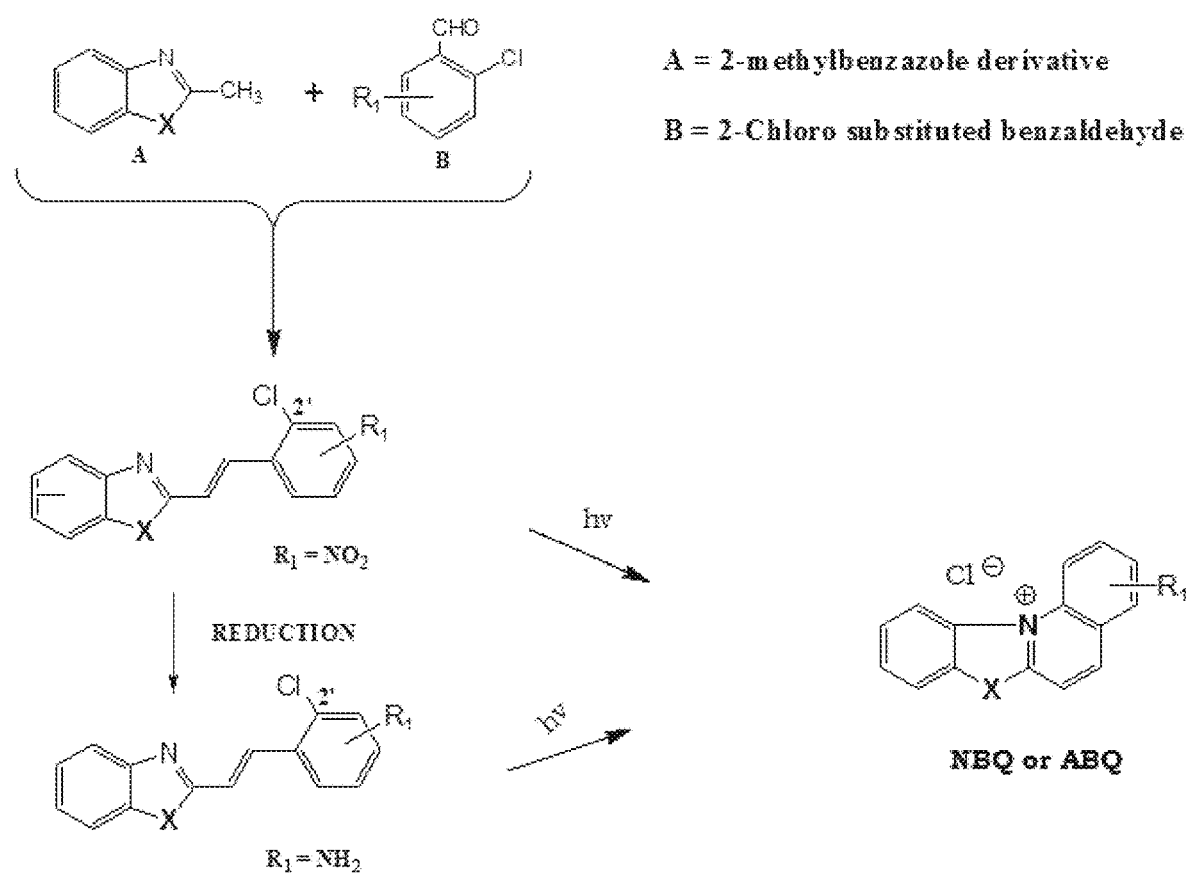
FIG. 36 shows the general procedure for the synthesis of 3-nitro- and 3-aminobenzimidazo[3,2-a]quinoliniun chlorides derivatives.

Synthesis: The synthesis of new benzimidazo[3,2-a]quinolinium chlorides (1, 1a, 2, and 2a) was achieved as shown in Scheme 2 and FIG. 36 as described earlier by us. The synthesis commences with the condensation of a benzimidazole derivative (A) with 2-chlorobenzaldhyde in boiling acetic anhydride to give a 2-chloro-5-nitrostyrylbenzimidazole ($R_1=NO_2$), reduction of the nitro group produces the corresponding 2-chloro-5-aminobenzimidazole derivative ($R_1=NH_2$). Photochemically induced cyclization of either $R_1=NO_2$ or $R_1=NH_2$, produces the desired NBQ or ABQ, respectively.

In this particular instance benzimidazole A corresponds to 1-(3,4,5-Trimethoxybenzyl)-2-methylbenzimidazole (6) or 1-(2,3,4-trimethoxybenzyl)-2-methylbenzimidazol (6a), respectively. The synthesis of 6 an 6a described in Scheme 3 follows a procedure similar to that described by Chang. Thus condensation of 6 or 6a with 2-chlorbenzaldehyde produced 1-(3,4,5-trimethoxybenzyl)- or 1-(2,3,4-trimethoxybenzyl)-2-(2-chloro-5-nitrostyryl)benzimidazolole (7 or 8, respectively). The reduction of 7 or 8 with nickel boride and hydrazine in methanol produced 7a or 8a, which upon photochemical cyclization produced benzimidazo[3,2-a]quinolinium chlorides (1, 1a, 2, and 2a).

Scheme 2. General procedure for the synthesis of 3-nitro- and 3-aminobenzimidazo[3,2-a]quinoliniun chlorides derivatives.

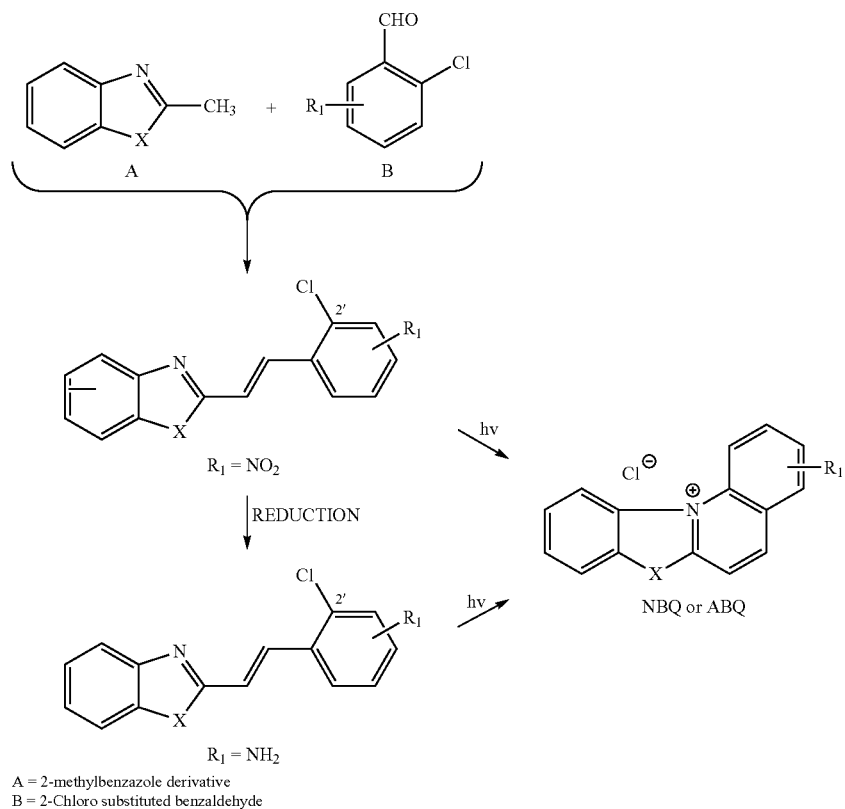

A = 2-methylbenzazole derivative
B = 2-Chloro substituted benzaldehyde

Figure 37:
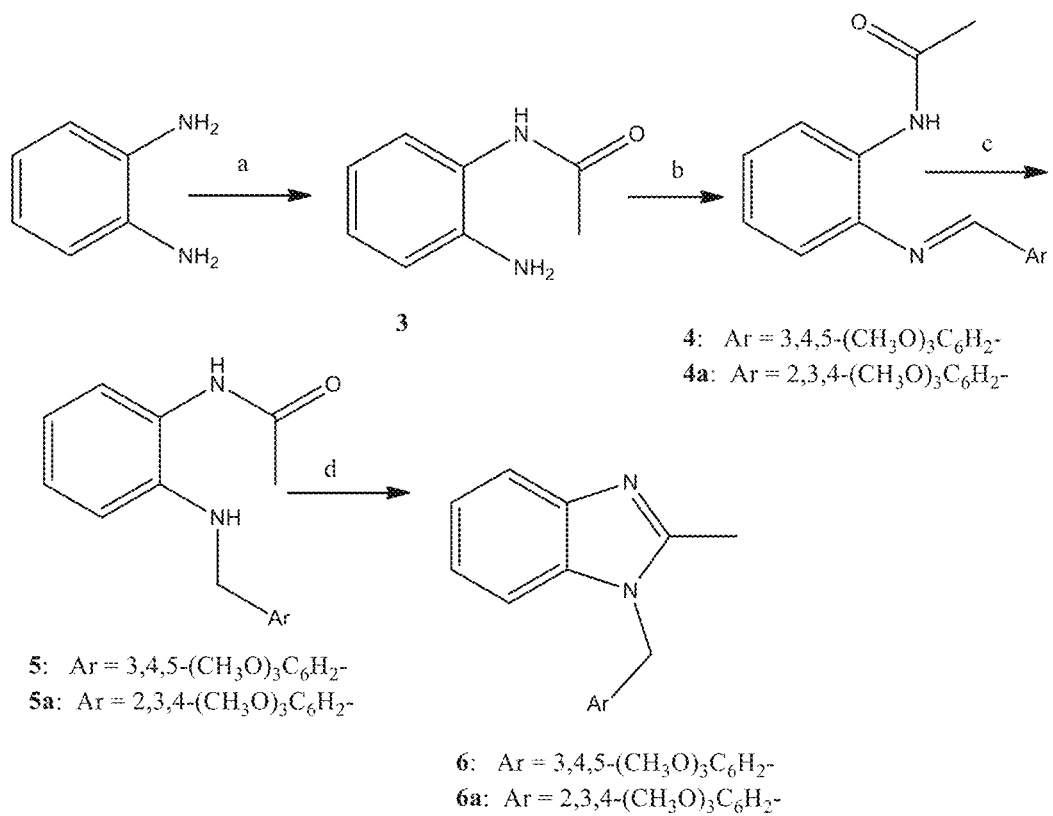

The general procedure for the synthesis of the required unknown benzimidazoles 6, and 6a is summarized in Scheme 3 and FIG. 37. The synthesis commences with 2-aminoacetanilide that is converted to 6 or 6a following the methodology described by Chang et al [4], where was converted to a N-[2-(3,4,5-trimethoxybenzylideneamino) phenyl]acetanilide (4) or N-[2-(2,3,4-trimethoxybenzylideneamino)phenyl]acetanilide (4a) by reaction with 3,4,5- or 2,3,4-trimethoxybenzaldehyde in dry methanol at room temperature. Reduction of either 4 or 4a with sodium borohydride in dry methanol at room temperature gave either 5 or 5a. The reaction of 5 or 5a with 4N HCl in ethanol at 50° C. for a period of 5 h gave the corresponding benzimidazoles 6 or 6a.

Scheme 3. Synthesis of benzimidazoles 6 and 6a.

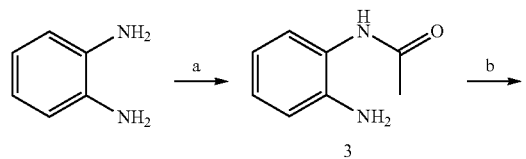

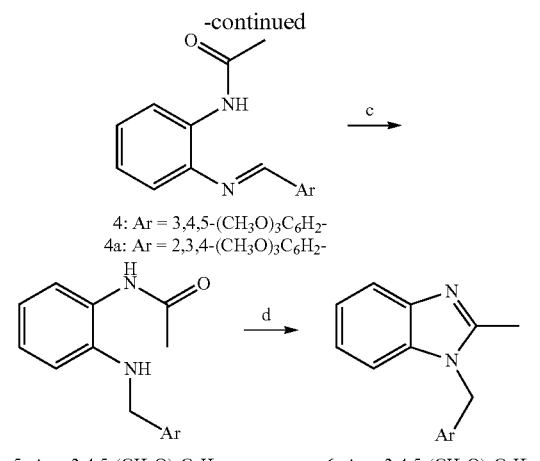

a. one molacetic anhydride in cold EtOAc. b. (for 4 or 4a, respectively) 3,4,5- or 2,3,4-trimethoxybenzaldehyde. c. sodium borohydride in dry methanol at rt. d. boiling acetic acid.

Experimental Section

All experiments were carried out in pre-dried glassware (2 h, 125° C.) under an open atmosphere, unless stated otherwise. The irradiations were conducted at room temperature using a Rayonet Photochemical Reactor fitted with 350 nm lamps. Melting points were determined in a capillary tube using a Melt-Temp apparatus. Description of the NMRs at the Molecular Science Research Center. The proton ($^1$H) and carbon-13 ($^{13}$C) NMR spectra were recorded using a Bruker AVANCE III HD equipped with a 5 mm CPQCI 1H-31P/13C/15N/D Z-GRD probe operating at frequency of 700.26 and 176.08 MHz for $^1$H and $^{13}$C, respectively; or a Bruker AVANCE III HD equipped with a 5 mm CPP BBO 500S1 BB-H&F-D-05 Z probe operating at frequency of 500.13 MHz and 125.75 MHz for $^1$H and $^{13}$C, respectively. The proton data were referenced to tetramethylsilane at δ 0.0 ppm, chloroform at δ 7.26 ppm or methyl sulfoxide at δ 2.49 ppm. The carbon-13 data were referenced to the center peak of deuteriochloroform at δ 77.0 ppm or the center peak of DMSO-d6 multiplet at δ 39.5 ppm. 2-Aminoacetanilide (3). To a magnetically stirred solution of 10.0 g (92.5 mmol) of o-phenylenediamine (1) in 150 mL of ethyl acetate maintained at 5° C. was added drop-wise, a cold solution of 9.43 mg (92.5 mmol) of acetic anhydride in 100 mL of ethyl acetate. The solution was stirred for an additional 20 min, and the precipitated solid was filtered under vacuum to give 5.24 g (37.8%) of a white solid: mp 132-133° C. The melting point and the $^1$H NMR (DMSO, 500 MHz) data correspond to the literature.

N-[2-(3,4,5-trimethoxybenzylideneamino)phenyl]acetanilide (4). Following the general procedure, a solution of 2.00 g (12.6 mmol) of 2-aminoacetanilide and 2.62 g (13.3 mmol) of 3,4,5-trimethoxybenzaldehyde in 75 mL of dry methanol was magnetically stirred at room temperature overnight. The precipitated solid was filtered and dried to give 4, mp 189-191° C. MS Calcd for $C_{18}H_{20}N_2O_4$: 328.1, found by ESIMS at m/z (M+H)$^+$329.3. This product was used for subsequent experiments.

N-[2-(3,4,5-trimethoxybenzylamino)phenyl]acetamide (5). To a magnetically stirred solution of 9.0 g (60.0 mmol) N-[2-(3,4,5-trimethoxybenzylideneamino)phenyl]acetanilide (4) in 75 mL of methanol at 5° C. was added pulverized sodium borohydride was slowly added until the mixture color turns white. Excess sodium borohydride was quenched by the addition of distilled water. The resulting mixture was extracted with ethyl acetate (3×50 mL), then washed with brine, dried over anhydrous MgSO$_4$ and finally filtered under vacuum to afford 5 in 80% yield (g), mp 134-136° C. MS Calcd for $C_{18}H_{22}N_2O_4$: 330.1, found by ESIMS at m/z (M+H)$^+$ 331.4. This product was used for subsequent experiments.

1-(3,4,5-Trimethoxybenzyl)-2-methylbenzimidazole (6). To a suspension of 1.0 g (3.0 mmol) 2-N-(3,4,5-trimethoxybenzylamino)acetamide (5) in ethanol (20 mL) was added 3 mL of 4N HCl. The suspension was heated at 50° C. for 5 h. The resulting solution was allowed to cool at room temperature and neutralized with ammonium hydroxide, extracted with ethyl acetate (3×50 mL), washed with brine, dried over anhydrous MgSO$_4$ and filtered under vacuum to afford 6, mp 104-106° C. $^1$H NMR (DMSO-d$_6$, 500 MHz) δ (ppm): 7.55 (dd, J=6.55, 2.50 Hz, 1H), 7.52 (dd, 6.55, 2.50, 1H), 7.16 (m, 2H), 6.48 (s, 2H, Aryl protons), 6.38 (s, 2H, ArCH$_2$—), 3.67 (s, 6H, 2OCH$_3$), 3.62 (s, 3H, OCH$_3$), 2.51 (s, 3H, CH$_3$). $^{13}$C-NMR (DMSO-d$_6$, 125 MHz) δ 153.6, 152.3, 142.8, 137.4, 135.8, 133.7, 122.1, 121.8, 118.7, 110.5, 60.6, 56.6, 56.4, 47.0, 14.2. Anal. Calcd for: $C_{18}H_{20}N_2O_3$: C, 69.21; H, 6.45; N, 8.97. Found: C, 69.25, H, 6.65, N, 8.90.

1-(3,4,5-Trimethoxybenzyl)-2-(2-chloro-5-nitrostyryl)benzimidazolole (7). Following the general procedure [10, 11], 1-(3,4,5-trimethoxybenzyl)-2-methylbenzimidazole (6), (14.7 g, 66.0 mmol) was condensed with 2-chloro-5-nitrobenzaldehyde (12.2 g, 66.0 mmol) in boiling acetic anhydride to yield 24.1 g (94%) of crude product, mp 184-186° C. $^1$H NMR (DMSO, 500 MHz) δ 8.96 (d, J=2.65 Hz, 1H), 7.86 (d, J=15.6 Hz, 1H), 7.72-7.68 (m, 2H), 7.28-7.26 (m, 2H), 6.63 (s, 2H), 5.73 (s, 2H), 3.66, (s, 6H, 2 CH$_3$), 3.60 (s, 3H, OCH$_3$). $^{13}$C-NMR (DMSO-d$_6$, 125 MHz) δ 153.4, 150.3, 147.3, 139.6, 137.5, 136.9, 133.4, 131.8, 129.5, 124.8, 123.4, 123.2, 122.5, 120.7, 119.7, 111.4, 105.2, 60.5, 56.3, 45.6. Anal. Calcd for $C_{25}H_{22}ClN_3O_5$: C, 62.57; H, 4.62; N, 8.76. Found: C, 62.53; H, 4.60; N, 8.71.

1-(3,4,5-Trimethoxybenzyl)-2-(2-chloro-5-aminostyryl)benzimidazolole (7a). This compound was obtained from the reduction of (E)-1-(3,4,5-trimethoxybenzyl)-(2'-chloro-5'-nitrostyryl)benzimidazole (7) (500 mg, 1.04 mmol) with nickel-boride and hydrazine in boiling methanol as described [11] to yield 8 (400 mg, 85%) as a yellow solid, mp 165-168° C. $^1$H NMR (DMSO, 700 MHz) δ 8.07 and 7.46 (AB Pattern, J=15.7 Hz, 2H), 7.67 (m, 1H), 7.63 (m, 1H), 7.45 (dd, J=9.0, 2.1 Hz, 1H), 7.23 (m, 2H), 7.18 (d, J=2.1 Hz, 1H), 7.15 (d, J=9.0 Hz, 1H), 7.12 (dd, J=9.0, 2.1 Hz, 1H), 6.52 (s, 2H), 5.52 (s, 2H), 4.92 (bs, NH$_2$) 3.59 (3H), 3.58 (s, 3H), 3.56 (s, 3H).

7-(3,4,5-trimethoxybenzyl)-3-nitrobenzimidazo[3,2-a]quinolinium chloride (1). 1-(3,4,5-Trimethoxybenzyl)-2-(2-chloro-5-nitrostyryl)benzimidazolole (7) (0.50 g, 1.3 mmol) was dissolved in 150 mL of a 2:2:1 (heptane:dioxane:bromobenzene) mixture and photolyzed as described [Patentes #2] to give the title compound as a bright yellow solid. $^1$H NMR (DMSO-d$_6$, 400 MHz) δ 9.47 (d, J=8.00 Hz, 1H), 9.42 (d, J=2.80 Hz, 1H), 9.25 (d, J=8.25 Hz, 1H), 9.07 (d, J=9.60 Hz, 1H),), 8.81 (m, 2H), 8.31 (d, J=9.60, 1H), 7.98 (m, 2H), 6.84 (s, 2H), 6.09 (s, 2H), 3.71 (s, 3H), 3.62 (s, 3H), 3.35 (s, 3H). $^{13}$C-NMR (DMSO-d$_6$, 100 MHz) δ 153.7, 145.4, 144.8, 140.5, 138.1, 137.1, 132.7, 129.9, 129.3, 128.8, 127.5, 127.1, 126.8, 124.8, 119.9, 117.4, 114.4, 112.0, 106.0, 60.47, 56.59, 48.4.

7-(3,4,5-Trimethoxybenzyl)-3-aminostyrylbenzimidazo[3,2-a]quinolinium chloride (1a). 1-(3,4,5-Trimethoxybenzyl)-2-(2-chloro-5-aminostyryl)benzimidazolole (8) (0.500 g, 1.11 mmol) was dissolved in 150 mL of a 2:2:1 heptane:dioxane:bromobenzene mixture and photolyzed as described [Zayas and Cox 2012, Patent 2] to give 8 (300 mg, 60% yield). $^1$H NMR (DMSO-d$_6$, 700 MHz) δ 9.05 (d, J=8.61, 1H), 8.89 (d, J=9.17 Hz, 1H), 8.56 (d, J=9.52, 1H), 8.31 (d, J=9.52, 1H), 8.17 (d, J=, 1H), 7.85 (m, 1H), 7.78 (m, 1H), 7.44 (dd, 2.66, 7.44 Hz, 1H), 7.27 (d, J=2.59 Hz, 1H), 6.77 (s, 2H), 5.93 (s, 3H), 3.67 (s, 6H), 3.60 (s, 3H). $^{13}$C-NMR (DMSO-d$_6$, 175 MHz) δ 153.1, 148.0, 141.5, 139.4, 137.4, 132.0, 130.0, 127.7, 125.8, 1256.5, 124.7, 121.4, 118.1, 117.9, 116.8, 113.0, 111.0, 108.3, 105.3, 59.8, 55.8, 47.4.

N-[2-(2,3,4-trimethoxybenzylideneamino)phenyl]acetanilide (4a). To a magnetically stirred solution of 2.00 g (13.3 mmol) of 2-aminoacetanilide (3) in 75 mL of dry methanol at 5° C. was added 2.62 g (13.3 mmol) of 2,3,4-trimethoxybenzaldehyde and left stirring overnight. The resulting precipitated solid was filtered under vacuum to afford 4a (80% yield, 3.49 g), mp 133-134° C. This product was used for subsequent experiments.

N-[2-(2,3,4-trimethoxybenzylamino)phenyl]acetamide (5a). To a solution of N-[2-(2,3,4-trimethoxybenzylideneamino)phenyl]acetanilide(4a) (3.0 g, 9.1 mmol) in 75 mL of methanol at 5° C. was added sodium borohydride was added drop-wise until the mixture color turns white. Excess sodium borohydride was quenched by the addition of distilled water. The resulting mixture was extracted with ethyl acetate (3×50 mL), then washed with brine, dried over anhydrous MgSO$_4$ and finally filtered under vacuum to afford 5a (85% yield, 2.55 g), mp 145-147° C. $^1$H NMR (DMSO-d$_6$, 500 MHz) δ 9.19 (s, 1H), 7.13 (J=7.55 Hz, 1H), 6.98 (m, 2H), 6.74 (d, J=8.60 Hz), 6.54 (AB Pattern, J=8.30), 5.31 (m, 1H), 4.24 (d, J=4.60 Hz), 3.85 (s, 3H), 3.77

(s, 3H), 3.76 (s, 3H), 2.05 (s, 3H. $^{13}$C-NMR (DMSO-d$_6$, 125 MHz) δ 169.2, 152.8, 151.6, 142.9, 142.1, 126.8, 126.5 125.3, 124.2, 123.0, 116.1, 111.5, 108.1, 61.2, 68.8, 56.2, 41.6, 23.8. This product was used for subsequent experiments.

1-(2,3,4-trimethoxybenzyl)-2-methylbenzimidazole (6a). A solution of N-[2-(2,3,4-trimethoxybenzylamino)phenyl] acetamide (5a) (6.50 g, 19.7 mmol) in 25.0 mL of acetic acid was refluxed for 5 hr. After cooling the reaction mixture was carefully neutralized with solid sodium hydrogen carbonate, and the reaction mixture was extracted with dichloromethane (3×50 mL), washed with saturated sodium chloride solution, dried over anhydrous sodium sulfate and concentrated under vacuum to yield 3.0 g (46% yield) of the desired product 6a as a white solid. Recrystallization from methanol gave pure (6a) as a white solid, mp 103-105° C., $^1$H NMR 500 MHz, CDCl$_3$) δ 7.88 (d, 1H, J=7.75 Hz), 7.49-7.37 (m, 3H), 6.59 (AB Pattern, J=8.50 Hz, 2H), 5.37 (s, 2H), 3.87 (s, 3H), 3.85, (s, 3H), 3.77 (s, 3H), 2.97 (s, 3H). $^{13}$C NMR 125 MHz, CDCl$_3$) δ 154.9, 151.6, 150.7, 142.1, 135.2, 125.2, 125.0, 123.3, 123.2 118.4, 116.3, 111.4, 107.0, 60.9, 60.7, 56.1, 44.5, 12.2. Anal. Calcd for: C$_{18}$H$_{20}$N$_2$O$_3$: C, 69.21; H, 6.45; N, 8.97. Found: C, 69.20; H, 6.40; N, 8.90.

1-(2,3,4-Trimethoxybenzyl)-2-(2-chloro-5-nitrostyryl) benzimidazolole (8). Following the general procedure [10, 11], 1-(2,3,4-trimethoxybenzyl)-2-methylbenzimidazole (6a), (4.0 g, 12.0 mmol) was condensed with 2-chloro-5-nitrobenzaldehyde (2.37 g, 12.0 mmol) in boiling acetic anhydride to yield 4.59 g (79.0%) of crude product. This was washed with acetone:hexane (1:1) and recrystallized from methanol to give a pale yellow solid, mp 202-204° C. $^1$H NMR (DMSO, 500 MHz) δ 8.93 (d, J=2.65 Hz), 8.19 (dd, J=8.80, 2.65 Hz, 1H), 8.18 (d, J=15.70 Hz, 1H), 7.99 (d, J=15.70, 1H), 7.86 (d, J=8.85, 1H), 7.70 (m, 1H), 7.24 (m, 1H), 6.75 AB Pattern, J=8.75 Hz, 2H), 5.69 (s, 2H), 3.73 (s, 3H, OCH$_3$), 3.73 (s, 3H, OCH$_3$), 3.72 (s, 3H, OCH$_3$). $^{13}$C-NMR (DMSO-d$_6$, 125 MHz) δ 153.8, 151.5, 150.4, 147.5, 143.3, 142.2, 139.6, 136.0, 135.5, 131.9, 128.9, 124.6, 123.4, 123.2, 123.0 122.7, 122.3, 121.1, 119.6 111.5, 108.3, 61.2, 60.7, 56.2, 42.4. Anal. Calcd for C$_{25}$H$_{22}$ClN$_3$O$_5$: C, 62.57; H, 4.62; N, 8.76. Found: C, 62.51; H, 4.59; N, 8.70.

7-(2,3,4-trimethoxybenzyl)-3-nitrobenzimidazo[3,2-a] quinolinium chloride (2). Compound 8 (328 mg (0.0683 mmol) was irradiated as described to give 100 mg (30% yield) of the title compound 2. $^1$H NMR (DMSO-d$_6$, 500 MHz) δ 9.45 (d, J=9.50 Hz, 1H), 9.41 (d, J=2.60 Hz, 1H), 9.18 (d, J=8.25 Hz, 1H), 9.06 (d, J=8.25 Hz, 1H), 8.79 (dd, J=2.55, 9.45 Hz, 1H), 8.70 (d, J=8.65 Hz, 1H), 7.9 (m, 2H), 7.29 (d, J=8.70, 1H), 7.79 (d, J=8.75 Hz, 1H), 6.06 (s, 2H), 3.71 (s, 3H), 3.70 (s, 3H), 3.52 (s, 3H).

1-(2,3,4-Trimethoxybenzyl)-2-(2-chloro-5-aminostyryl) benzimidazolole (8a). This compound was obtained from the reduction of (E)-1-(3,4,5-trimethoxybenzyl)-(2'-chloro-5'-nitrostyryl)benzimidazole (7a), 1.50 g (3.13 mmol), with nickel-boride and hydrazine in boiling methanol as described [11] to yield (70% yield, 1.0 g) of (8a) as a yellow solid, mp 155-157° C. $^1$H NMR (DMSO-d$_6$, 500 MHz) δ 8.08 (d, J=15.65 Hz, 1H), 7.67 (dd, J=7.40, 1.65 Hz, 1H), 7.48 (dd, J=7.40, 1.65 Hz, 1H), 7.40 (d, J=15.7, 1H), 7.20 (m, 2H), 7.15 (d, J=8.60 Hz, 1H), 7.20 (d, J=2.40 Hz, 1H), 6.75 (d, J=8.65 Hz, 1H), 6.65 (d, J=8.65 Hz, 1H), 6.62 (dd, J=8.70, 2.45 Hz, 1H), 5.56 (s, 2H), 5.29 bs, 2H), 3.73 (s, 6H, 2 OCH$_3$), 3.72 (s, 3H, OCH$_3$). $^{13}$C-NMR (DMSO-d$_6$, 125 MHz) δ 153.7, 151.4, 148.4, 143.3, 142.2, 135.5, 133.8, 132.1, 130.5, 123.0, 122.8, 122.7, 122.6, 119.2, 117.2, 116.6, 111.7, 111.2, 108.2, 61.2, 60.8, 42.5.

7-(2,3,4-Trimethoxybenzyl)-3-aminostyrylbenzimidazo [3,2-a]quinolinium chloride (2a). This compound was obtained from the irradiation of 35 mg (7.78×10$^{-2}$ mmol) of 8a as described [ref]. to yield (30 mg, 85% yield) of 2a. $^1$H NMR (DMSO-d$_6$, 500 MHz) δ 9.06 (d, J=8.50, 1H), 8.90 (d, J=9.15 Hz, 1H), 8.58 (d, J=9.55 Hz, 1H), 8.26 (d, J=9.60 Hz, 1H), 8.12 (d, J=8.25 Hz), 7.85 (t, J=7.50 Hz, 1H), 7.78 (t, J=7.50 Hz, 1H), 7.45 (dd, J=7.00, 1.55 Hz, 1H), 7.28 (bs, 1H), 7.20 (d, J=8.70 Hz, 1H), 6.77 (d, 8.70 Hz, 1H), 6.03 (bs, 2H, NH$_2$), 5.93 (s 2H, ArCH$_2$), 3.77 (s, 3H, OCH$_3$), 3.71 (s, 3H, OCH$_3$), 3.64 (s, 3H, OCH$_3$). Anal. Calcd for: C$_{25}$H$_{24}$ClN$_3$O$_3$: C, 66.74; H, 5.38; N, 9.34. Found: C, 66.55; H, 5.47; N, 9.08.

Biological Activities

Cell culture conditions: The cell cultures utilized in this study were human colorectal adenocarcinoma COLO-205 (ATCC CCL-222). Cultures were maintained in RPMI 1640 media (ATCC, Manassas Va.) supplemented with 10% fetal bovine serum (ATCC) maintained at 37° C. with 95% air and 5% CO$_2$.

Apoptosis Analysis by Annexin V Expression: The annexin V assay allows detection of the migration phosphatidylserine (PS) to the exterior surface of cells, a characteristic event in apoptotic cells. Approximately 2.5×10$^6$ cells were treated for 24 hours with 10 μM and 20 μM doses of the BQ test compounds. Controls used in all assays were camptothecin 10 μM, and vehicle (DMSO). After a 24-hour exposure, cells were stained with the annexin V conjugate, and propidium iodide (Biotium, Hayward, Calif.). Samples were analyzed by using the Nucleo Counter NC3000 system annexin V assay (Chemometec, Allerød, Denmark). This system allows for measurement and quantification of stained cells. A one-way ANOVA with post hoc Tukey test was also performed for all assays using GraphPad Prism version 6.

DNA Fragmentation: DNA Fragmentation can be used as a marker for detection of cells undergoing apoptosis. This enzyme mediated event can be quantified by measuring DNA fragments. The Nucleo Counter NC3000 assay is based on removal of small DNA fragments and retention of 4',6-diamidino-2-phenylindole (DAPI) stained higher weight fragments. After treatment with BQ's at the test doses, cells were fixed with 70% ethanol for at least 24 hours, stained with 1 μg/ml DAPI, and analyzed using the NC3000 instrument measuring DAPI intensity.

Mitochondrial Membrane Permeability: Mitochondria permeability is central in the cell death process. The Nucleocounter NC3000 preset mitochondrial potential assay was used. Approximately 1×10$^6$ cells were stained with 5,5',6, 6'-Tetrachloro-1,1',3,3'-tetraethyl-imidacarbocyanine iodide (JC-1) and 1 μg/ml DAPI and analyzed in the NC3000. depolarized cells will fluoresce green while cells with stable mitochondrial membrane potential will fluoresce orange. The change in ratio of green to orange fluorescence will determine the permeability state of the samples.

Figure 25:
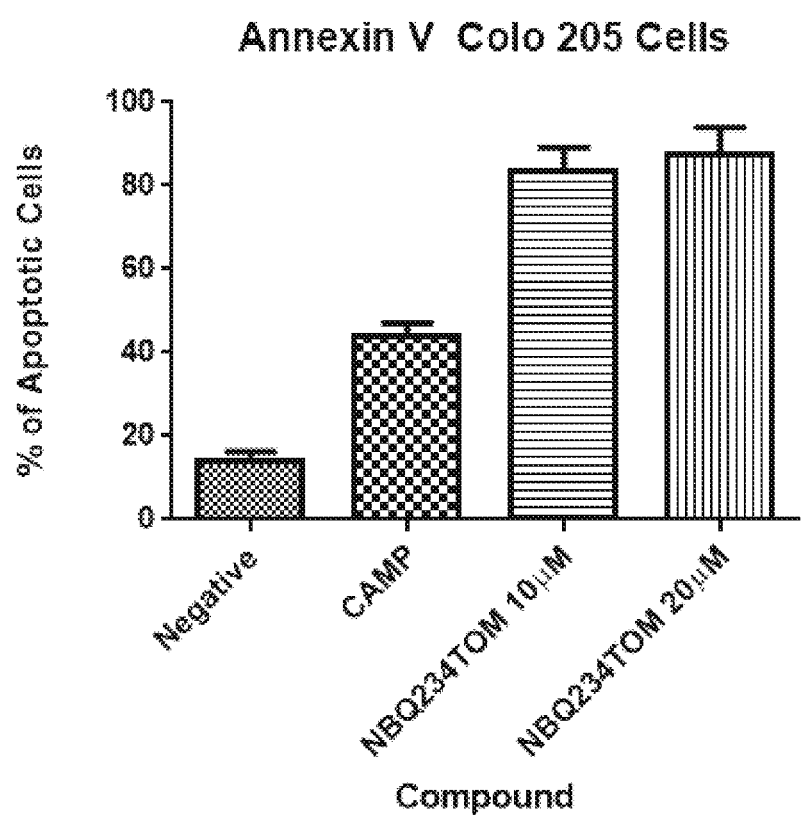
FIG. 25 shows NBQ 234 TOM apoptosis analysis by Annexin V.

FIG. 25 discloses NBQ 234 TOM apoptosis analysis. Apoptosis analysis by Annexin V expression in colo 205 cancer cells after treating with NBQ234 at 10 μM and 20 μM in comparison to positive and negative control. Tested compound clearly presented a higher apoptotic induction at both doses. At 10 µM an 83.7% of apoptotic cells was detected while at 20 µM, 87.5% of cells were apoptotic.

Figure 26:
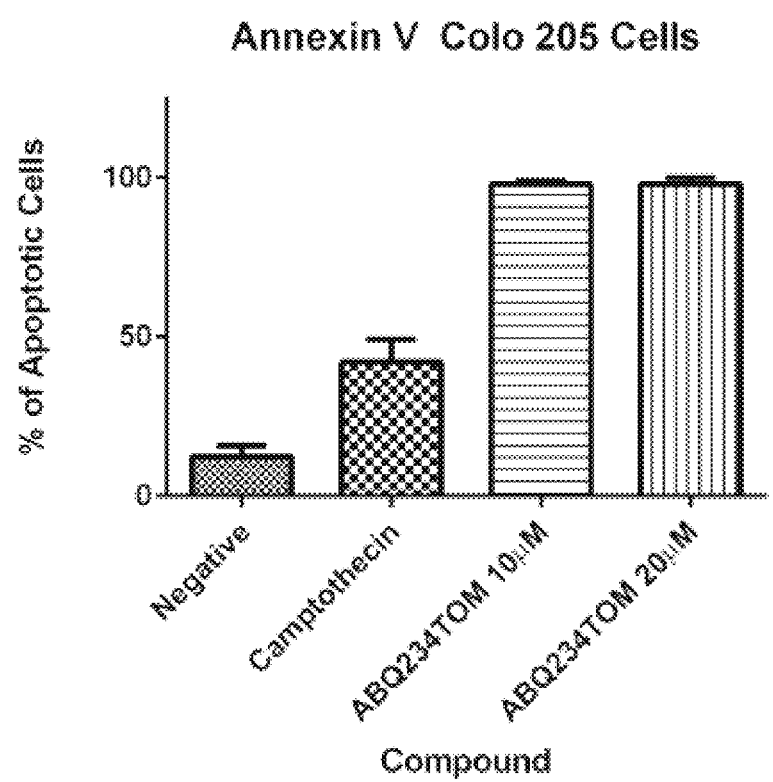
FIG. 26 shows ABQ 234 TOM apoptosis analysis by Annexin V.

FIG. 26 discloses ABQ 234 TOM apoptosis analysis. Apoptosis analysis by Annexin V expression in colo 205 cancer cells after treating with ABQ234 at 10 µM and 20 µM in comparison to positive and negative control. Tested compound clearly presented a higher apoptotic induction at both doses with 91% of cells apoptotic.

Figure 27:
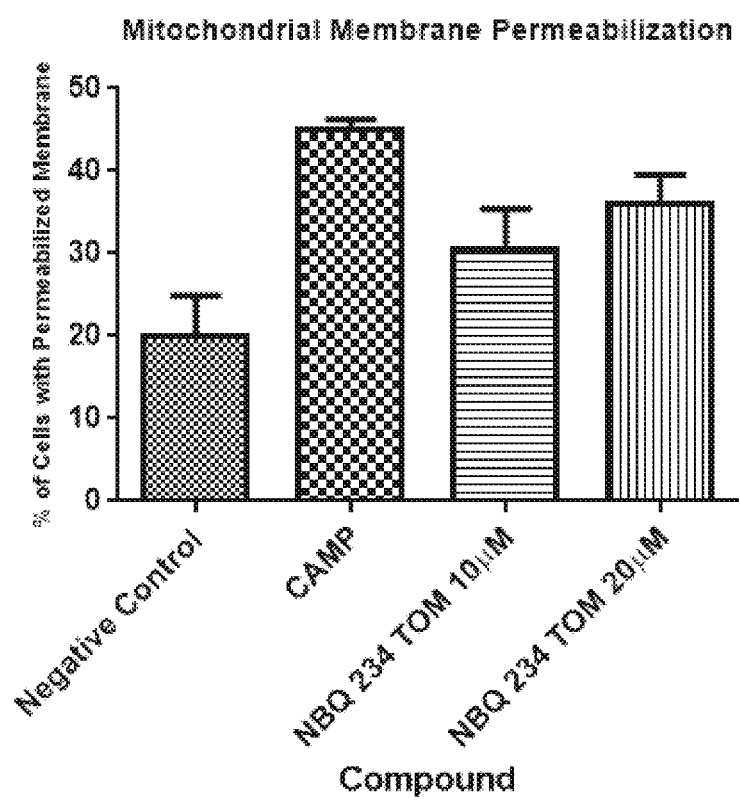
FIG. 27 shows mitochondrial membrane permeabilization for NBQ234TOM.

FIG. 27 discloses mitochondrial membrane permeabilization for NBQ234TOM. Cells treated with NBQ 234 TOM presented higher mitochondrial permeabilization in comparison with the negative control (water as vehicle) but lower than cells treated with the positive control camptothecin.

Figure 28:
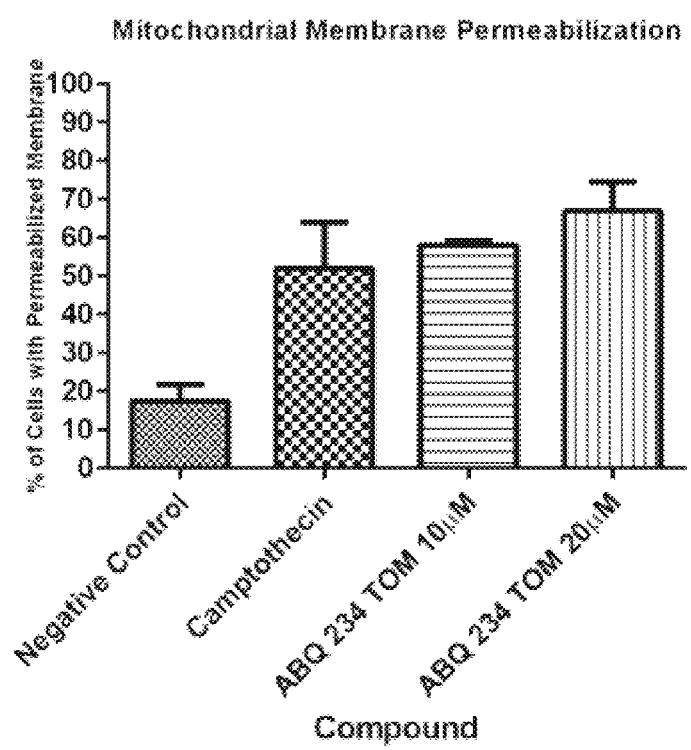
FIG. 28 shows mitochondrial membrane permeabilization for ABQ234TOM.

FIG. 28 discloses mitochondrial membrane permeabilization for ABQ234TOM. Cells treated with ABQ 234 TOM presented higher mitochondrial permeabilization in comparison with the negative control (water as vehicle) and similar to the positive control camptothecin.

Figure 29:
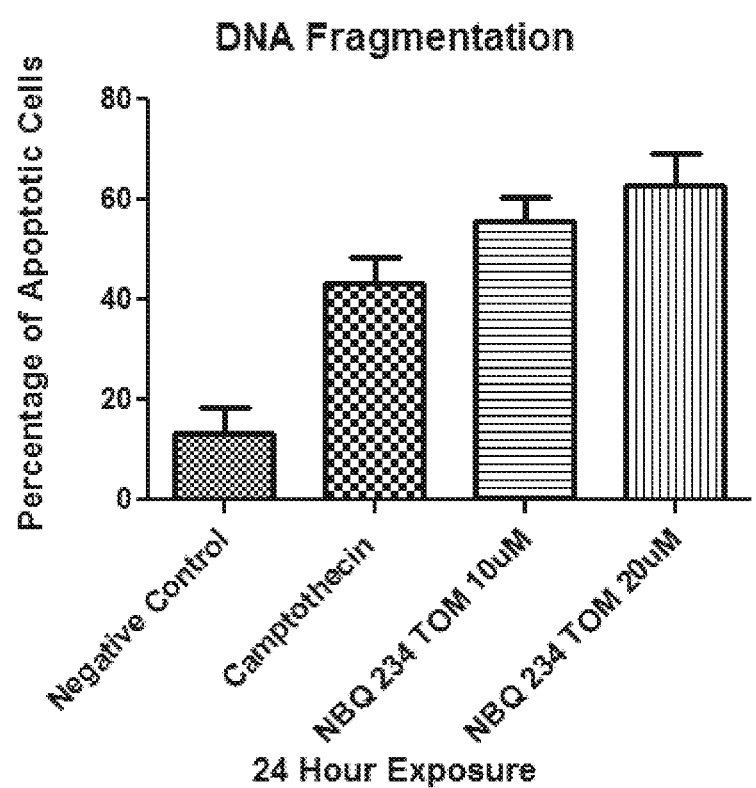
FIG. 29 shows DNA fragmentation induction results for NBQ234TOM.

FIG. 29 discloses DNA fragmentation induction results for NBQ234TOM. Cells treated with NBQ 234 TOM presented higher DNA fragmentation in comparison with the negative control (water as vehicle) and higher than the positive control camptothecin.

Figure 30:
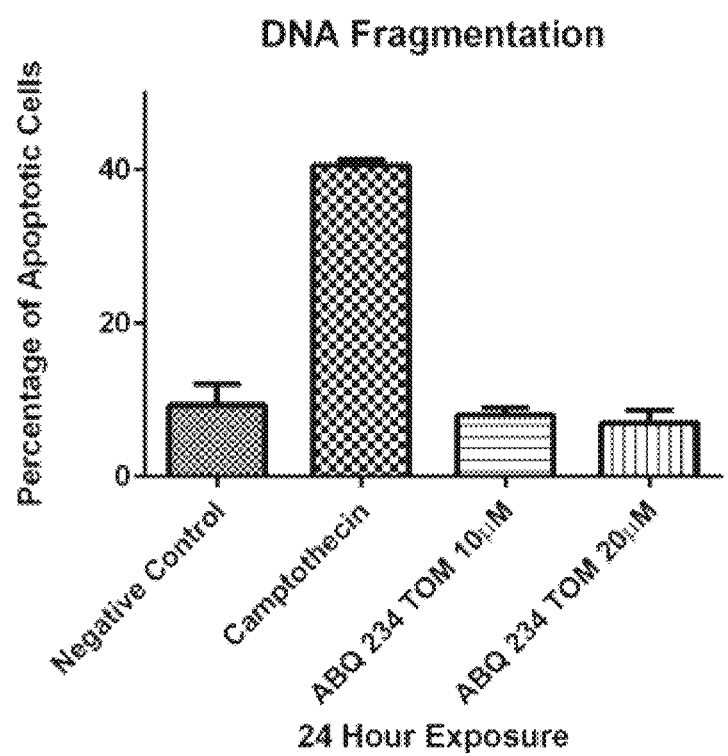
FIG. 30 shows DNA fragmentation induction results for ABQ234TOM.
Figure 31:
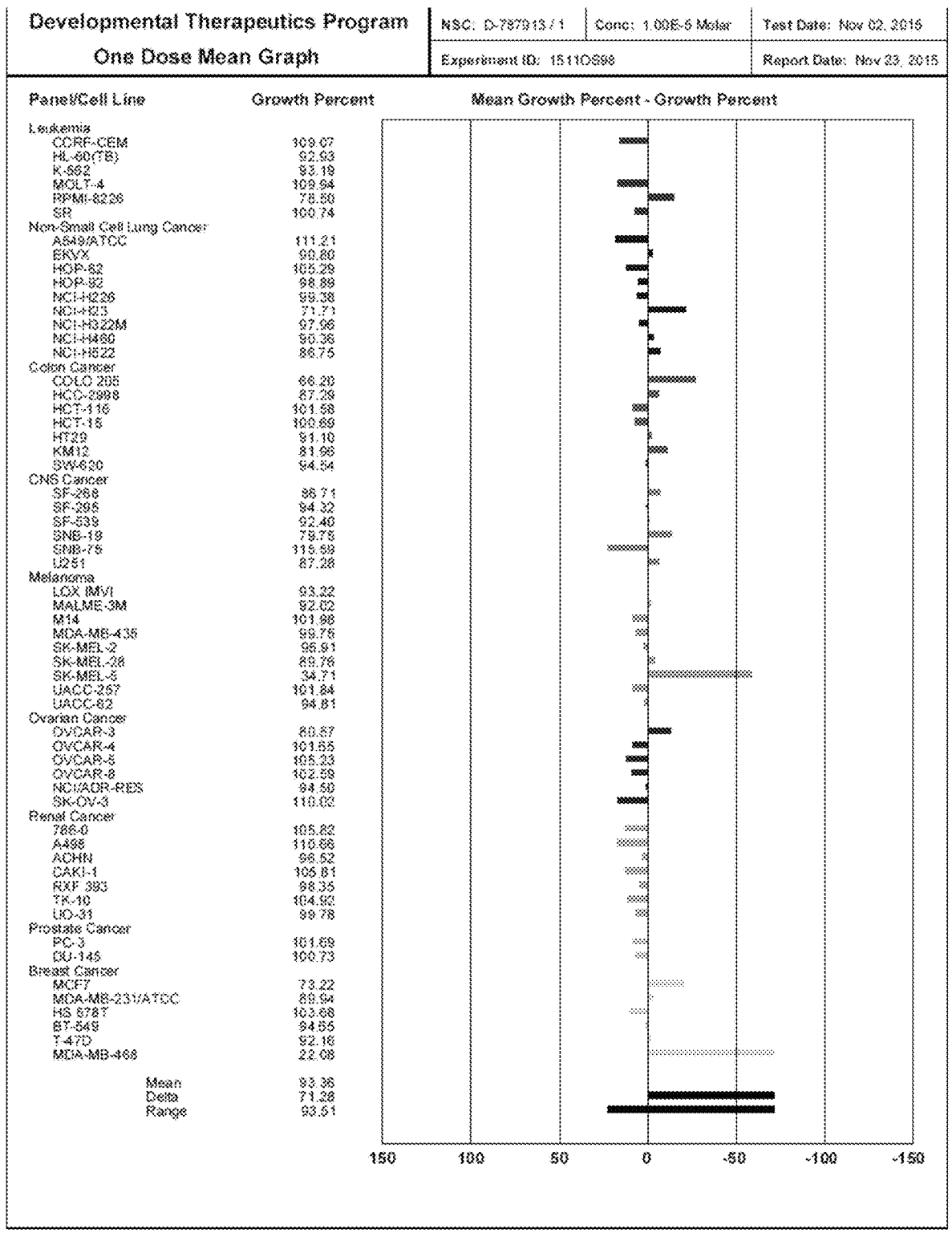
FIG. 31 shows one dose mean data graph for NBQ-48-3-234-TOM-787913 in the NCI 60 human cancer cell line screen.
Figure 32:
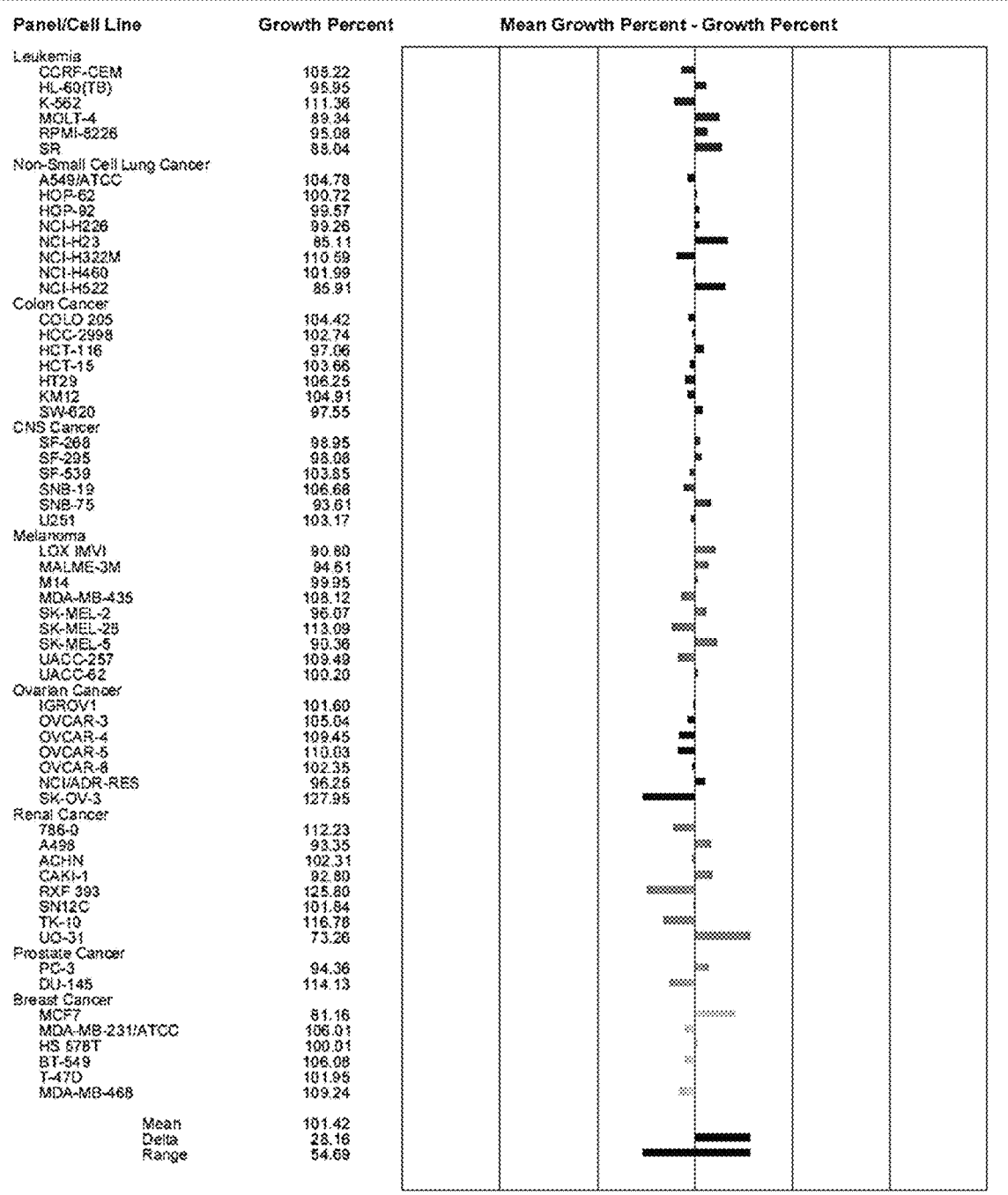
FIG. 32 shows one dose mean data graph for NBQ-48-345-TOM-777569 in the NCI 60 human cancer cell line screen.
Figure 33:
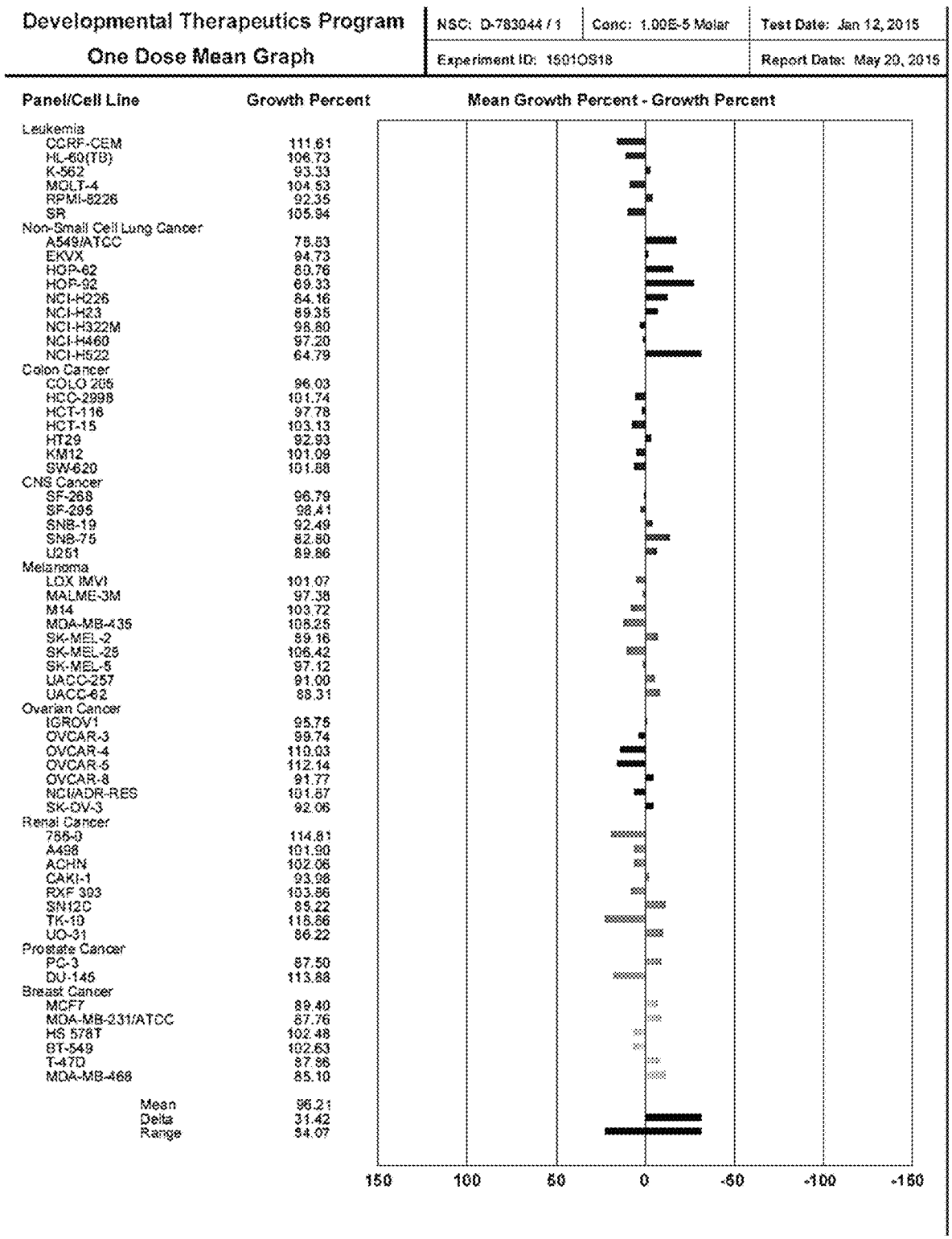
FIG. 33 shows one dose mean data graph for ABQ-48-345-TOM-783044 in the NCI 60 human cancer cell line screen.
Figure 34:
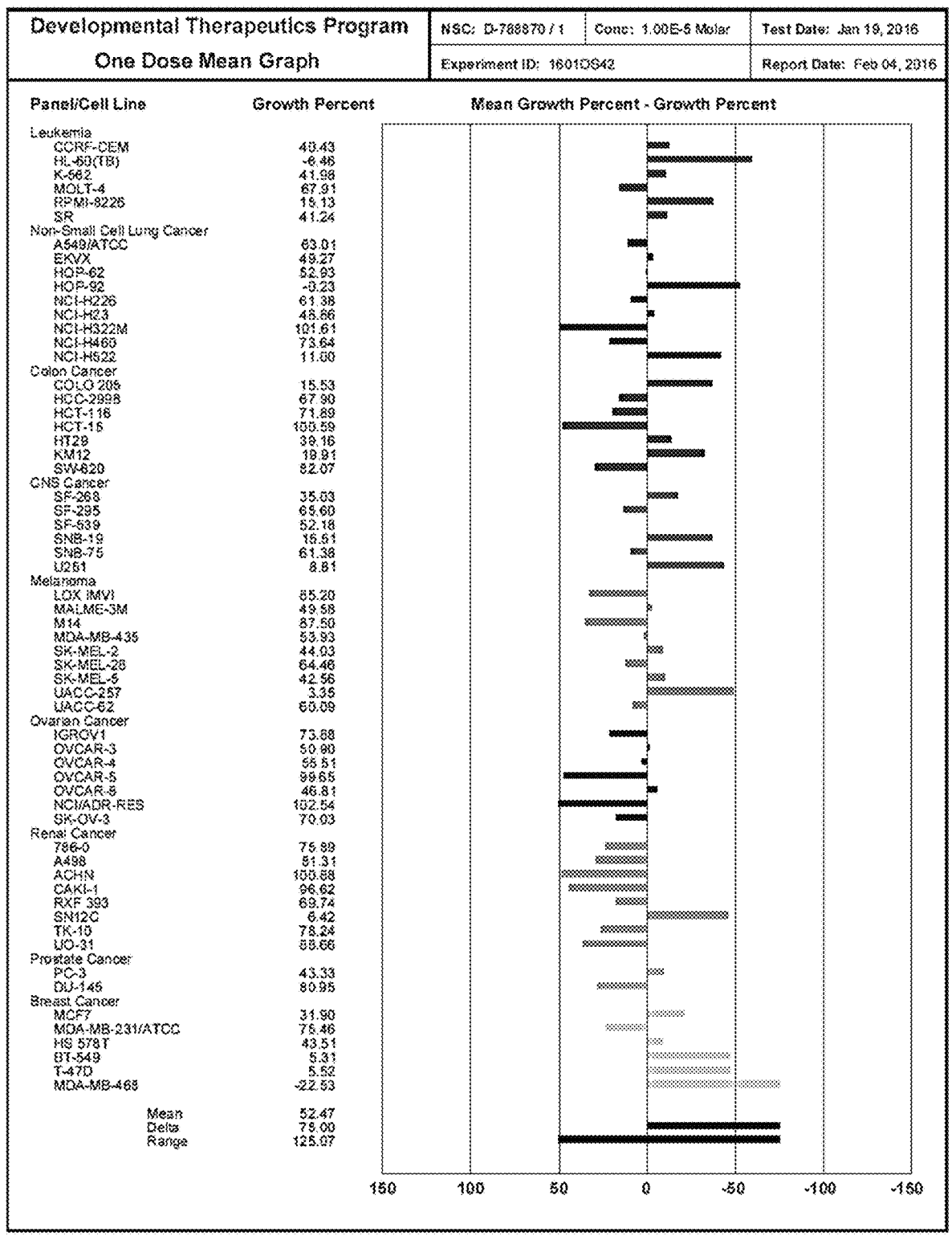
FIG. 34 shows one dose mean data graph for ABQ-48-234-TOM-788870 in the NCI 60 human cancer cell line screen.

FIG. 30 discloses DNA fragmentation induction results for ABQ234TOM. Cells treated with ABQ 234 TOM did not present evidence of DNA fragmentation in comparison with the negative control (water as vehicle) and positive control camptothecin.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

What is claimed is:

1. A benzazolo[3,2-a]alquinolinium chloride salt compound of formula

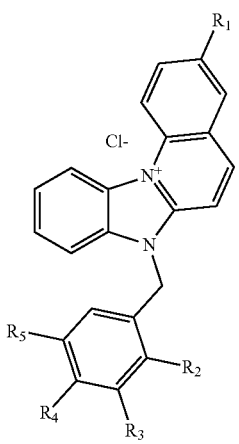

wherein $R_1$ is selected from a group consisting of 3-$NH_2$ and 3-$NO_2$; $R_2$ is selected from a group consisting of hydrogen and $OCH_3$; $R_3$ is $OCH_3$; $R_4$ is $OCH_3$; and $R_5$ is hydrogen, when $R_2$ is $OCH_3$, and $OCH_3$, when $R_2$ is hydrogen.

2. A pharmaceutical composition, comprising the compound of claim 1 and, a pharmaceutically acceptable carrier or excipient.

3. The compound of claim 1, wherein $R_2$ is $OCH_3$; $R_3$ is $OCH_3$; $R_4$ is $OCH_3$; and $R_5$ is hydrogen.

4. A pharmaceutical composition, comprising the compound of claim 3 and, a pharmaceutically acceptable carrier or excipient.

5. The compound of claim 1, wherein $R_2$ is hydrogen; $R_3$ is $OCH_3$; $R_4$ is $OCH_3$; and $R_5$ is $OCH_3$.

6. A pharmaceutical composition, comprising the compound of claim 5 and, a pharmaceutically acceptable carrier or excipient.

7. The compound of claim 1, wherein $R_1$ is 3-$NH_2$; $R_2$ is $OCH_3$; $R_3$ is $OCH_3$; $R_4$ is $OCH_3$; and $R_5$ is hydrogen.

8. A pharmaceutical composition, comprising the compound of claim 7 and, a pharmaceutically acceptable carrier or excipient.

9. The compound of claim 1, wherein, $R_1$ is 3-$NO_2$; $R_2$ is $OCH_3$; $R_3$ is $OCH_3$; $R_4$ is $OCH_3$; and $R_5$ is hydrogen.

10. A pharmaceutical composition, comprising the compound of claim 9 and, a pharmaceutically acceptable carrier or excipient.

11. The compound of claim 1, wherein $R_1$ is 3-$NO_2$; $R_2$ is hydrogen; $R_3$ is $OCH_3$; $R_4$ is $OCH_3$; and $R_5$ is $OCH_3$.

12. A pharmaceutical composition, comprising the compound of claim 11 and, a pharmaceutically acceptable carrier or excipient.

13. The compound of claim 1, wherein $R_1$ is 3-$NH_2$; $R_2$ is hydrogen; $R_3$ is $OCH_3$; $R_4$ is $OCH_3$; and $R_5$ is $OCH_3$.

14. A pharmaceutical composition, comprising the compound of claim 13 and, a pharmaceutically acceptable carrier or excipient.

15. A method of treating a cancer selected from the group consisting of leukemia, non-small cell lung cancer, colon cancer, central nervous system cancer, melanoma, renal cancer, prostate cancer, and breast cancer in a mammal, comprising: administering to said mammal, a therapeutically effective amount of the compound of claim 7.

16. The method of claim 15, wherein the cancer is leukemia and wherein the mammal is a human.

17. The method of claim 15, wherein the cancer is non-small cell lung cancer and wherein the mammal is a human.

18. The method of claim 15, wherein the cancer is breast cancer and wherein the mammals a human.

19. A method for reducing cell growth of at least a cancer cell selected from a group consisting of HL-60(TB), K-562, RPMI-8226, EKVX, NCI-H23, NCI-H460, NCI-H522, COLO 205, HCC-2998, HT29, KM12, SW-620, SF-268, SF-295, SF-539, SNB-19, U251, LOX IMVI, MALME-3M, SK-MEL-2, SK-MEL-28, SK-MEL-5, UACC-62, OVCAR-3, NCI/ADR-RES, MCF7, MDA-MB-231/ATCC, BT-549, T-47D and MDA-MB-468 in a mammal, comprising: administering to said mammal, a therapeutically effective amount of the compound of claim 9.

20. A method for reducing cell growth of at least a cancer cell selected from a group consisting of HL-60(TB), MOLT-4, RPMI-8226, SR, NCI-H23, NCI-H522, SNB-75, LOX IMVI, MALME-3M, SK-MEL-5, A498, CAKI-1, UO-31, PC-3 and MCF7 in a mammal, comprising: administering to said mammal, a therapeutically effective amount of the compound of claim 11.

21. A method for reducing cell growth of at least a cancer cell selected from a group consisting of K-562, RPMI-8226, A549/ATCC, EKVX, HOP-62, HOP-92, NCI-H226, NCI-H23, NCI-H522, COLO 205, HT29, SNB-75, U251, SK-MEL-2, UACC-257, UACC-62, IGROV1, OVCAR-8, SV-OV-3,CAKI-1, SN12C, UO-31, PC-3, MCF7, MDA-MB-231/ATCC, T-47D and MDA-MB-468 in a mammal, comprising: administering said mammal, a therapeutically effective amount of the compound of claim 13.

* * * * *